US010282841B1

(12) United States Patent
Parsons-Wingerter et al.

(10) Patent No.: US 10,282,841 B1
(45) Date of Patent: May 7, 2019

(54) BIOINFORMATIC ANALYSIS OF VASCULAR PATTERNING

(71) Applicant: The United States of America as Represented by the Administrator of the National Aeronautics and Space Administration, Washington, DC (US)

(72) Inventors: Patricia A. Parsons-Wingerter, Los Altos, CA (US); Mary B. Vickerman, Cleveland, OH (US)

(73) Assignee: The United States of America as Represented by the Administrator of the NASA, Washington, DC (US)

( * ) Notice: Subject to any disclaimer, the term of this patent is extended or adjusted under 35 U.S.C. 154(b) by 84 days.

(21) Appl. No.: 15/213,175

(22) Filed: Jul. 18, 2016

Related U.S. Application Data

(63) Continuation-in-part of application No. 14/666,162, filed on Mar. 23, 2015, which is a continuation of application No. 13/339,521, filed on Dec. 29, 2011.

(60) Provisional application No. 61/429,357, filed on Jan. 3, 2011, provisional application No. 62/193,275, filed on Jul. 6, 2015.

(51) Int. Cl.
*G06K 9/00* (2006.01)
*G06T 7/00* (2017.01)
*G06T 7/40* (2017.01)
*A61B 3/12* (2006.01)
*G16B 45/00* (2019.01)

(52) U.S. Cl.
CPC .......... *G06T 7/0014* (2013.01); *A61B 3/1241* (2013.01); *G06T 7/408* (2013.01); *G16B 45/00* (2019.02); *G06T 2207/10024* (2013.01); *G06T 2207/20072* (2013.01); *G06T 2207/30104* (2013.01)

(58) Field of Classification Search
CPC ..... G06T 7/0014; G06T 7/408; A61B 3/1241; G06F 19/26
See application file for complete search history.

(56) References Cited

PUBLICATIONS

Wenzel, Carol L., Qian Hester, and Jim Mattsson. "Identification of genes expressed in vascular tissues using NPA-induced vascular overgrowth in Arabidopsis." Plant and cell physiology 49.3 (2008): 457-468. (Year: 2008).*
Balasubramanian, S. et al. "Automatic Localization and Segmentation of Blood Vessels, Optic Disc, and Macula in Digital Fundus Images." Advances in Communication Systems and Electrical Engineering. Springer US, 2008. 543-564.
(Continued)

*Primary Examiner* — Nirav G Patel
(74) *Attorney, Agent, or Firm* — Meredith K. Blasingame; Robert M. Padilla; Mark P. Dvorscak

(57) ABSTRACT

Biometric analysis of vascular patterning may be performed in 3D and 2D as an integrative biomarker of complex molecular and mechanical signaling. The vascular patterning may facilitate the coordination of essentially unlimited numbers of bioinformatics dimensions for specific molecular and other co-localizations with spatiotemporal dimensions of vascular morphology. The vascular patterning may also apply geometric principles of translational versus rotational principles for vascular branching to support the transformation of VESGEN 2D to VESGEN 3D.

20 Claims, 20 Drawing Sheets
(13 of 20 Drawing Sheet(s) Filed in Color)

(56) References Cited

PUBLICATIONS

Parsons-Wingerter, P. et al. "Generational analysis reveals that TGF-131 inhibits the rate of angiogenesis in vivo by selective decrease in the number of new vessels." Microvascular Research 59.2 (2000): 221-232.
Vickerman, M. et al. "VESGEN 2D: Automated, User-Interactive Software for Quantification and Mapping of Angiogenic and Lymphangiogenic Trees and Networks." Anatomical Record (Hoboken), Mar. 2009; 292(3): 320-332.
Parsons-Wingerter P. et al., "For Application to Human Spaceflight and ISS Experiments: VESGEN Mapping of Microvascular Network Remodeling during Intestinal Inflammation," Gravitational Space Biology Bull. Oct. 2012, 26 (2):2-12.
Chen X. et al., "Probiotic Yeast Inhibits VEGFR Signaling and Angiogenesis in Intestinal Inflammation," PloS One 8 (5):e64227 (May 13, 2013).
Parsons-Wingerter, P. et al. "Fibroblast Growth Factor-2 Selectively Stimulates Angiogenesis of Small Vessels in Arterial Tree," Arterioscler Thromb Vasc Biol. 2000; 20:1250-1256.
Parsons-Wingerter, P. et al. "Generational Analysis Reveals That TGF-61 Inhibits the Rate of Angiogenesis in Vivo by Selective Decrease in the number of New Vessels." Microvascular Research 59, 221-232 (2000).
Parsons-Wingerter, P. et al. "A VEGF 165-Induced Phenotypic Switch from Increased Vessel Density to Increased Vessel Diameter and Increased Endothelial NOS Activity." Microvascular Research 72 (2006) 91-100.
McKay, T. et al. "Selective Inhibition of Angiogenesis in Small Blood Vessels and Decrease in Vessel Diameter Throughout the Vascular Tree by Triamcinolone Acetonide." Investigative Ophthalmology & Visual Science, Mar. 2008, vol. 49, No. 3, 1184-1190.
Liu, H. et al."Role of VEGF and Tissue Hypoxia in Patterning of Neural and Vascular Cells Recruited to the Embryonic Heart." Developmental Dynamics 238:2760-2769 (2009).
NASA Tech Briefs, "Quantifying Therapeutic and Diagnostic Efficacy in 2D Microvascular Images" Nov. 27-28, 2009.
Vickerman, M. et al. "VESGEN 2D: Automated, User-Interactive Software for Vascular Quantification and Mapping of Angiogenic and Lymphangiogenic Trees and Networks." Anat Rec (Hoboken) Mar. 2009; 292(3): 320-332.
Parsons-Wingerter, P. et al. "Mapping and Quantification of Vascular Branching in Plants, Animals and Humans by VEGEN Software." NASA Glenn Research Center, 2010.
Parsons-Wingerter, P. et al. "Oscillation of Angiogenesis with Vascular Dropout in Diabetic Retinopathy by VESsel Generation (VESGEN)." Investigative Ophthalmology & Visual Science, Jan. 2010, vol. 51, No. 1, 498-507.
Parsons-Wingerter, P. et al. "Informative Mapping by VESGEN Analysis of Venation Branching Pattern in Plant Leaves Such as *Arabidopsis thaliana*." Gravitational and Space Biology, vol. 25 (1) Sep. 2011, 69-71.
Parsons-Wingerter, P. et al. "VESGEN Mapping of Adult Leaf Venation Patterning in *Arabidopsis* for ISS Applications." 28th Annual Meeting, American Society for Gravitational and Space Research, Concurrent Technical Session V: Plants (Part I), Nov. 2012, New Orleans, LA, USA.
Parsons-Wingerter, P. et al. "New Therapeutic Window of Regenerative Opportunity in Diabetic Retinopathy by VESGEN Analysis." NASA Glenn Research Center, 2012.
NASA Tech Briefs, "VESGEN Software for Mapping and Quantification of Vascular Regulators" Mar. 13, 2012.
Parsons-Wingerter, P. et al. "Mapping of Wing Venation Phenotypes in Drosophilia from Hairless H-C2 Overexpression for Modeling Environmental Stressors." 29th Annual Meeting, American Society for Gravitational and Space Research, 5th Meeting of the International Symposium for Physical Sciences in Space, Concurrent Sessions 29-33, Nov. 2013, Orlando, FL, USA.
Parsons-Wingerter, P. et al. "Modeling Environmental Stressors by Mapping of Mutant Phenotypes in Wing Venation of *Drosophilia* Such as Overexpression of Hairless H-C2." NASA Glenn Research Center, 2013.
Parsons-Wingerter, P. et al. "Mapping by VESGEN of Leaf Venation Patterning in *Arabidopsis thaliana* with Bioinformatic Dimensions of Gene Expression." Gravitational and Space Research, vol. 2(1) Aug. 2014, 68-80.

\* cited by examiner

BIOINFORMATIC ANALYSIS OF VASCULAR PATTERNING

CROSS-REFERENCE TO RELATED APPLICATIONS

This application is a continuation-in-part of U.S. Nonprovisional patent application Ser. No. 14/666,162 filed Mar. 23, 2015, which is a continuation of U.S. Nonprovisional patent application Ser. No. 13/339,521 filed Dec. 29, 2011, which claims the benefit of U.S. Provisional Patent Application No. 61/429,357 filed Jan. 3, 2011. This application also claims the benefit of U.S. Provisional Patent Application No. 62/193,275 filed Jul. 16, 2015. The subject matter of these earlier filed applications is hereby incorporated by reference in its entirety.

ORIGIN OF THE INVENTION

The invention described herein was made by employees of the United States Government and may be manufactured and used by or for the Government of the United States of America for governmental purposes without the payment of any royalties thereon or therefore.

FIELD

The present invention generally pertains to vascular patterning, and more specifically, to biometric analysis of vascular patterning in 3D and 2D as an integrative biomarker of complex molecular and mechanical signaling.

BACKGROUND

For some decades, a great need in biomedical research has been the insightful mapping and quantification of vascular remodeling for vascular-dependent diseases such as cancer, diabetes, and coronary vessel disease. Vascular patterning serves as an integrative biomarker principle of multi-scale signaling by complex molecular pathways and mechanical forces. However, the tissue-specific complexity of successive branching generations of multi-scale, fractal-based vascular systems is difficult to characterize and measure. For many decades, vascular systems were assessed within histological sections and other microscopic images as small round circles. One technical challenge is the many length scales encompassed by the branching vascular system. The diameter of the human aorta, for example, is approximately 3.7 centimeters upstream of many successive vessel bifurcations down to the end-stage capillaries (diameter of approximately 10 micrometers). Another vascular mapping challenge is tissue-specific patterning. Patterning of the highly permeable liver sinusoidal capillaries characterized by small avascular spaces, for example, is very different from the thin, essentially impermeable brain capillaries with large avascular spaces that establish the blood brain barrier (BBB).

When viewed as a technical advantage, however, tissue-specific vascular patterning offers an integrative biomarker principle for multi-scale signaling by complex molecular pathways and mechanical forces, and is therefore be useful for pathological, physiological, and therapeutic applications in biomedical and biological research, including ecology. This is due, in part, to the fractal-based fluid mechanics of complex vascular branching observed even in arterial river systems that support efficient filling of tissues or other spaces by branching aqueous transport systems. For example, the human body contains approximately 50,000 protein molecules that constantly react and interact via complicated metabolic, immunological, and other regulatory pathways, in addition to signaling by numerous other molecular families, such as DNA, RNA, lipids (fats), and steroid hormones. Scientists therefore combine sophisticated chemical analysis of phenomena such as variable gene expression by modern genomics with localized expression maps of genes and other molecules generated by clinical and microscopic tissue imaging, including images of the vasculature. The microscopic maps of molecular localization within tissues are necessary for revealing and consequently understanding the anatomical location and function of these molecules and sub-molecular moieties.

Vascular systems are required by all higher terrestrial life forms, including humans, other vertebrates, insects and higher land plants, to achieve chemical transport and communication between spatially distant cells. As two widely different examples that are nonetheless representative of higher metazoan life forms, virtually every cell in the human body must reside within approximately 500 micrometers (microns) of a capillary blood vessel for life support and functional performance. The leaf venation patterns of dicots (higher land plants) such as oak, maple, and *Arabidopsis thaliana* (thale cress) are unique, and therefore accepted by botanists as taxonomic/phylogenetic identifiers of individual species. NASA's fractal-based VESsel GENeration Analysis (VESGEN) software was therefore developed as a research and technology discovery tool for automated mapping and quantification of tissue-specific remodeling vascular patterns from microscopic and clinical images.

VESGEN was first developed for the analysis of vascular patterning as a semi-automatic Matlab™ prototype by innovator P. Parsons. The software is based on her original experimental observations in angiogenesis research that each molecular stimulator or inhibitor of vascular growth and remodeling, including VEGF, bFGF, TGf-beta1, angiostatin, and triamcinolone acetonide, induces an informative fingerprint or signature vascular pattern that is both spatio-temporally unique and an integrative readout of complex signaling. Past, current, and future applications include vascular-dependent human disease, such as astronaut health complications, diabetes, cancer and coronary vessel disease, experimental animal models, and plant leaves. Without the growth of new blood vessels (i.e., angiogenesis) that enable tumor growth and metastasis, most tumors would remain microscopically small and not become a medical problem. Excessive, abnormal neovascularization and/or vascular dropout and leakage is the major cause of blindness in diabetic retinopathy (DR) and age-related macular degeneration (AMD). Remodeling vasculature provides an insightful read-out of dominant molecular signaling when mapped and quantified by the innovative VESGEN software. Normalization of the vasculature is determined from the response of vascular pattern to therapeutic testing. Numerous disclosures, publications, and peer-reviewed research grant awards document the ongoing development of VESGEN as an innovative systems analysis of vascular patterning.

The three basic types of vascular morphology determined by molecular and mechanical signaling are branching vascular trees (at the scale of larger vessels), continuously connected vascular networks (at the scale of smaller capillary (reticular) vessels), and tree-network composites. These three types of vascular morphology are further modulated into characteristic vascular patterns as tissue-specific and organism-specific structures, such as the human/vertebrate retina, and species-specific vascular patterns in the leaves of higher (dicot) land plants. Typically, in vertebrate (e.g., human) tissues, a major arterial tree branches by successive, complex, irregular vessel bifurcations down to the level of the capillary network, which is the site of metabolic, immune, and other functional exchanges of the blood with the host tissue. Reacted blood is collected by the branching venous tree for transport back to the heart and lungs. Binary (black/white) image representations of 2D trees, networks, and tree-network composites at differing levels of image resolution are currently mapped and quantified automatically by the VESGEN software. Using VESGEN to analyze ophthalmic clinical vascular images, a potential paradigm shift was recently introduced to the understanding and therapeutic development of early-stage progression to provide new regenerative opportunities for human diabetic retinopathy (DR), the major blinding disease for working-aged adults. VESGEN mapped and quantified surprising, homeostatic-like vascular regeneration at an early stage when the vessels grow much more normally than at the late, highly abnormal, neovascularization stage that causes blindness.

Currently, there is a strong emphasis in biomedical research to identify useful biomarkers that characterize both pathological progression and therapeutic intervention, especially when the markers are highly specific and quantifiable. The discoveries on fingerprint or signature vascular patterns by molecular signaling (both endogenous and therapeutic) illustrate that vascular patterning offers one useful, insightful biomarker for the biomedical research and technology toolbox. With VESGEN, in vivo models of vascular patterning were analyzed for angiogenesis, lymphangiogenesis, and intravital blood flow from cellular/molecular levels to higher system levels that include a murine model of infant retinopathy of prematurity (ROP), developing and pathological coronary and placental-like vessel models, progressive intestinal inflammation, growing murine tumors, genetic mutations in the fruit fly wing, and other pathological, physiological, and therapeutically treated tissues of transgenic mice or avian embryos, as well as developing leaves in the major model organism for plant genetics, *Arabidopsis thaliana*.

VESGEN uses 8-neighbor pixel connectivity techniques of image processing to analyze the effects of vascular therapeutics and regulators on blood vessel form and function. Moreover, NASA's mandated enterprise—the long-term human exploration of space, including manned missions to Mars—is currently very challenging due to fundamental astronaut health impairments. These include cardiovascular alterations (CVA) such as the hypothesized increased intracranial pressure associated with well-documented post-spaceflight retinal damage, as a recently discovered high-priority effect of microgravity spaceflight, and therefore present a new NASA-defined bioastronautics risk factor. VESGEN technology was therefore developed and proposed as a novel informative tool for assessing changes to retinal vessels after spaceflight and in human bedrest studies that mimic effects of the microgravity space environment.

Although there is previous work published by other researchers that has to some extent measured vessel density or vascular fractal dimension, no other software has achieved the comprehensive, fractal-based, automated, user-interactive analysis of the three basic vascular morphologies (trees, networks, and tree-network composites) based on sectioning the branching tree and mapping the sections into branching generations. VESGEN 2D has already been applied to and documented successfully for important applications in clinical diagnostic images of the human retina and experimental studies of vascular regulators/therapeutics in the avian chorioallantoic membrane (CAM) and yolk sac, the genetically engineered rodent retina and heart, and other 2D tissue types. VESGEN 2D is a mature beta-level software requested by researchers around the world for many vascular applications.

Typically, VESGEN maps up to twelve (or sometimes more—up to 99 are currently allowed) generations of vascular branching (G1, G12) that may originate from a single parent vessel or multiple parent vessels. Quantification parameters include associated repertoires of vessel diameter, length, number, branch points, density, and fractal dimension (and more), specified to specific branching generations. VESGEN vascular mappings, and hence VESGEN quantification, are based on a defined system of physiological and anatomical rules for fractal-based vascular branching and vessel networks that support aqueous continuity requirements. However, an improved version of VESGEN that facilitates the coordination of essentially unlimited numbers of bioinformatics dimensions for specific molecular and other co-localizations with spatiotemporal dimensions of vascular morphology, and/or that applies geometric principles of translational versus rotational principles for vascular branching to support the transformation of VESGEN 2D to VESGEN 3D, may be beneficial.

SUMMARY

A method of analyzing vascular changes in an image may include the steps of converting the image to a binarized image and geometrically characterizing a vascular pattern based on at least one of physiological branching and networking principles in the binarized image using a software program. The method may further include the step of measuring density of vessels from the geometrically characterized vascular pattern by utilizing the software program.

A method of analyzing leaf venation of a plant leaf may include the steps of obtaining an image of the plant leaf displaying vascular system of the leaf, converting the image of the plant leaf into a binarized image, and analyzing the binarized image using a vascular tree-network composite option of a software program. The method may further include the steps of automatically mapping the venation pattern of the plant leaf using the software program, and measuring the venation pattern using the software program.

A method of analyzing vascular changes in a retina may include the steps of obtaining a fluorescein angiography or other clinical ophthalmic image of a vasculature of the retina, processing the fluorescein angiography image into a binary image, and separating vascular patterns of the binary image into arterial and venous vascular tree patterns. The method may further include automatically classifying a plurality of branching generations within the arterial vascular patterns and the venous vascular patterns, and measuring density of vessels from the classified arterial vascular patterns and venous vascular patterns.

Certain embodiments of the present invention may provide solutions to the problems and needs in the art that have not yet been fully identified, appreciated, or solved by conventional vascular patterning technologies. For example, some embodiments of the present invention pertain to vascular patterning that facilitates the coordination of essentially unlimited numbers of bioinformatics dimensions for specific molecular and other co-localizations with spatiotemporal dimensions of vascular morphology, and/or that applies geometric principles of translational versus rotational principles for vascular branching to support the transformation of VESGEN 2D to VESGEN 3D.

In an embodiment, a computer-implemented method includes receiving, by a computing system, two inputs comprising a binary map of a vascular pattern and a grayscale image of co-localized molecular expression and mapping, by the computing system, the binary vascular pattern into branching generations by sequential creation, and then coordinate analysis, of a series of image transformations. The computer-implemented method also includes superimposing, by the computing system, a final mapping of specific vessel generations onto the grayscale image of co-localized molecular expression to assign regions of molecular expression to specific vascular branching generations, and to avascular areas within the tissue. The computer-implemented method further includes analyzing, by the computing system, grayscale intensity of areas of molecular expression co-localized to specific vessel branching generations by a histogram frequency approach. Additionally, the computer-implemented method includes displaying, by the computing system, a plurality of bioinformatic dimensions on a display.

In another embodiment, a computer program is embodied on a non-transitory computer-readable medium. The program is configured to cause at least one processor to generate a plurality of bioinformatic dimensions of single molecular expression as co-localized with spatial and temporally evolving dimensions of branching vessel morphology from the vascular image that map to specific changes in expression patterns measured by polymerase chain reaction (PCR)-based omics analyses of single molecular expression. The computer program is also configured to cause the at least one processor to display the plurality of bioinformatic dimensions on a display.

In yet another embodiment, a computing system includes memory storing computer program instructions and at least one processor configured to execute the computer program instructions. The instructions are configured to cause the at least one processor to receive two inputs comprising a binary map of a vascular pattern and a grayscale image of co-localized molecular expression and map the binary vascular pattern into branching generations by sequential creation, and then coordinate analysis, of a series of image transformations.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

In order that the advantages of certain embodiments of the invention will be readily understood, a more particular description of the invention briefly described above will be rendered by reference to specific embodiments that are illustrated in the appended drawings. While it should be understood that these drawings depict only typical embodiments of the invention and are not therefore to be considered to be limiting of its scope, the invention will be described and explained with additional specificity and detail through the use of the accompanying drawings, in which.

DETAILED DESCRIPTION OF THE EMBODIMENTS

Reference will now be made in detail to exemplary embodiments of the present invention, examples of which are illustrated in the accompanying drawings. It is to be understood that other embodiments may be utilized and structural and functional changes may be made without departing from the respective scope of the invention. Moreover, features of the various embodiments may be combined or altered without departing from the scope of the invention. As such, the following description is presented by way of illustration only and should not limit in any way the various alternatives and modifications that may be made to the illustrated embodiments and still be within the spirit and scope of the invention.

Figure 1:
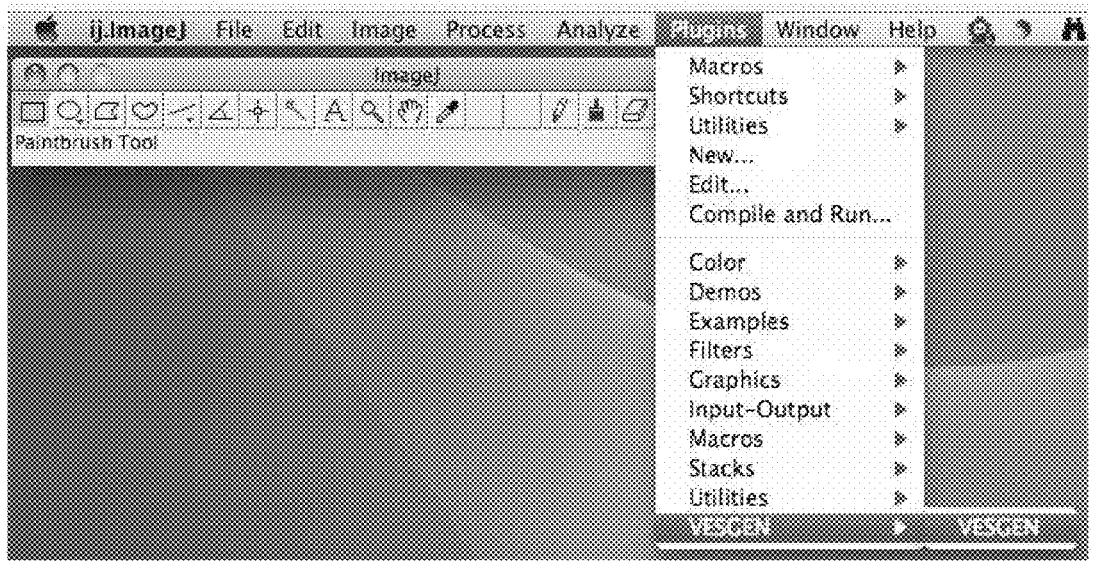
FIG. 1 is an exemplary screen shot of some embodiments of a VESGEN system.
Figure 2A:
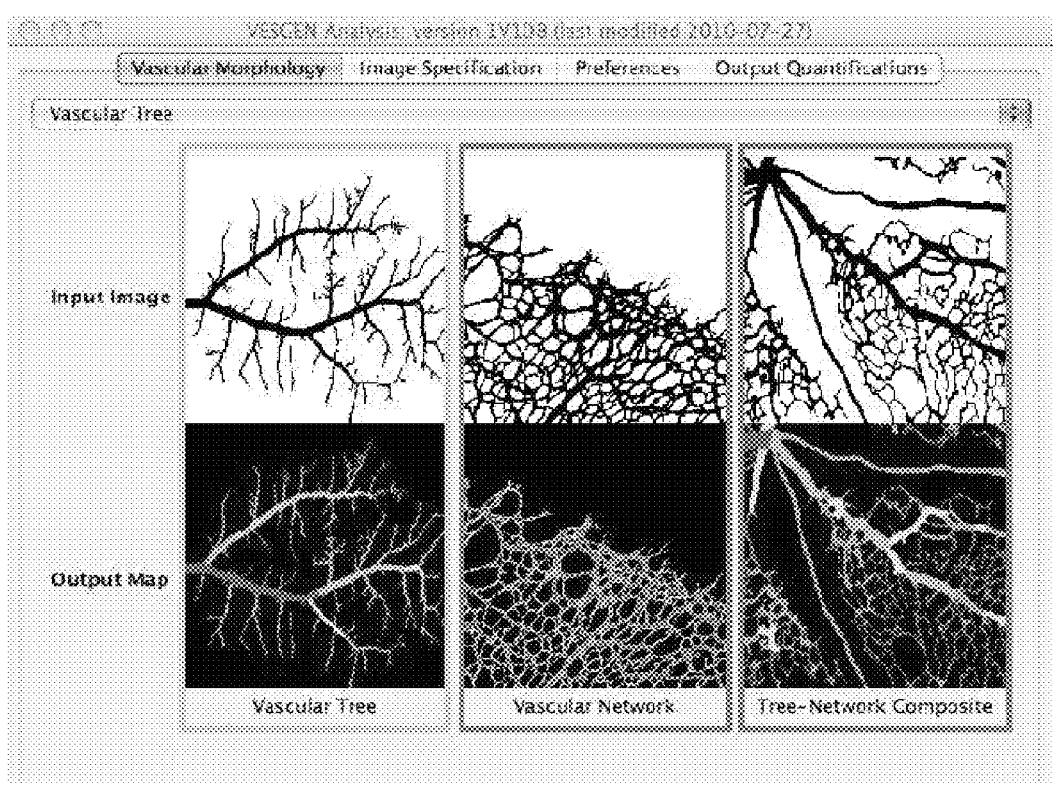
FIG. 2A is an exemplary screen shot of some embodiments of the VESGEN system of a selection of vascular morphology type.
Figure 2B:
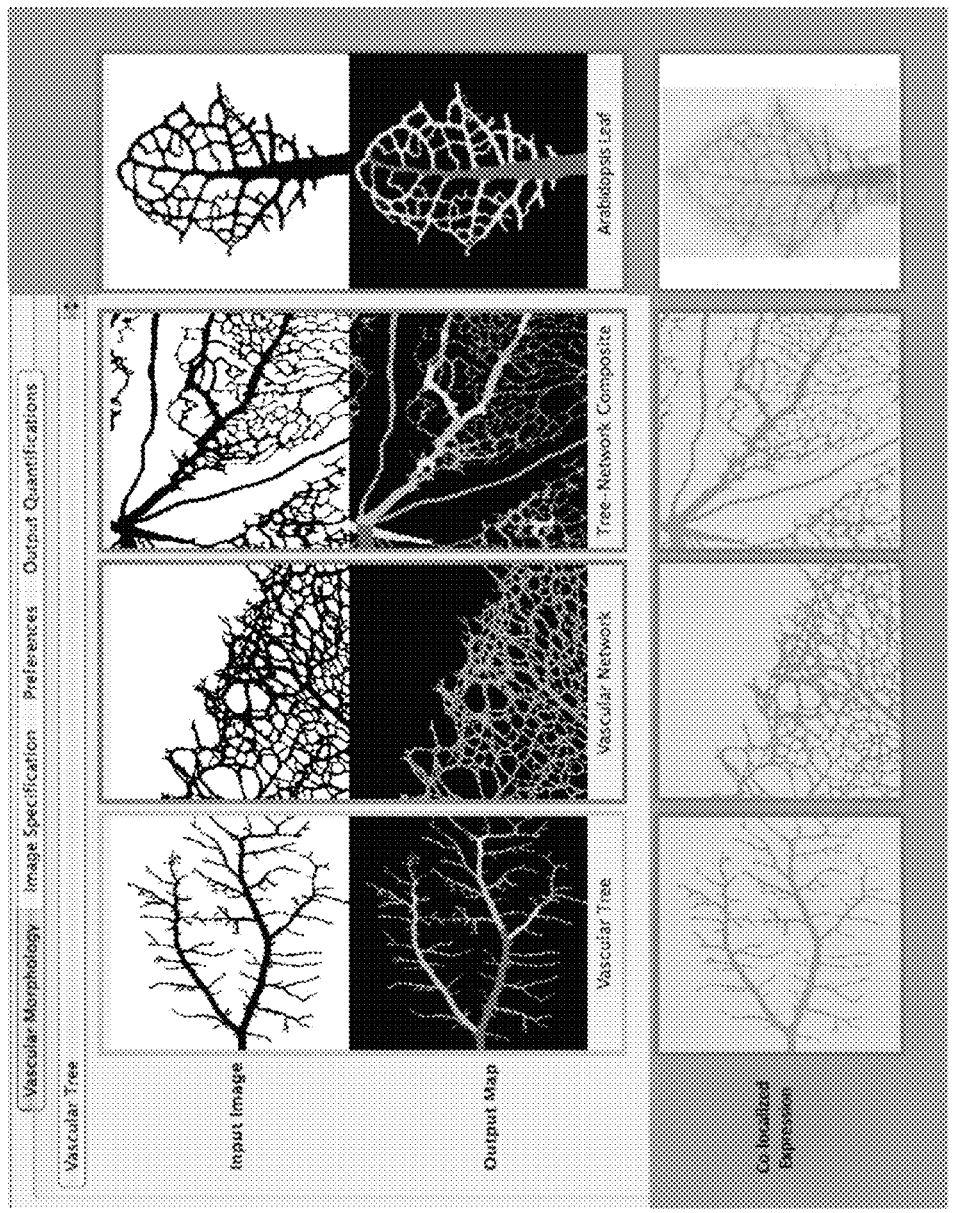
FIG. 2B is another exemplary screen shot of some embodiments of the VESGEN system.

Vessel generation analysis software system (hereinafter the "VESGEN system") may include a user-interactive research computer code that may be used to automatically map and quantify at least three types of microvascular morphology based on physiological principles that include branching vascular trees, continuously connected vascular networks, and vascular tree-network composite structures. An exemplary screen shot of the VESGEN system is shown in FIG. 1. By way of a non-limiting example, the VESGEN system may be used for mapping and quantification of vascular morphological events according to fractal-based vascular branching generation an exemplary screen shot of the VESGEN system is shown in FIG. 2A. The VESGEN system may be used in a variety of applications, including, without limitation where the analysis of vascular branching generation is desired. By way of a non-limiting example, the VESGEN system may: (i) provide for increased understanding and quantification of the effects of vascular therapeutics and regulators on blood vessel form and function; (ii) quantification of therapeutic and diagnostic efficacy assessed in microvascular images; (iii) predictive modeling of therapeutic efficacy in microvascular application; (iv) be used for analysis of progression in vascular-dependent diseases to identify new therapeutic opportunities and therapeutic development in organs such as the brain and bone; and (v) detect and analyze the first branching generation (parent) vessel when that vessel originates at a region of interest located within the image. Also, the VESGEN system may be used in space biology for bioinformatics and *Arabidopsis* leaf analyses. As shown in FIG. 2B, the screenshot includes an expanded interface region (Green, or gray if viewed without color). In the expanded interface region, the molecular staining (labeling) appears in turquoise (or gray if viewed without color). The VESGEN interface (background, gray) presents three analysis options to the user: Vascular Tree (selected here in gold), Vascular Network and Tree Network Composite. Additional capabilities are illustrated with green background: *Arabidopsis* Leaf, and Co-Localized Bioinformatic Expression of genes, proteins or other molecules such as microRNAs (miRNAs).

The VESGEN system may be easily distributable, may be capable of running on many different computer platforms, and may readily be utilized by researchers in many different fields. More specifically, the VESGEN system may be an automated, user-interactive computer software program that may analyze and quantify the effects of vascular therapeutics and regulators on microvascular form and function by, among other things, analyzing important vessel morphology parameters. The VESGEN system may assist a researcher with quantifying by measurement of change in key parameters of microvascular architecture, which may assist in observing therapeutically induced corrections to pathological microvascular morphology, and pathological vascular disease progression in general.

The VESGEN system's user interactive capabilities may guide the user through each required step of the analysis process via a concise user interface. The user interface may provide the appropriate direction and guidance to the user in a concise user-friendly manner, which may provide general automation to the VESGEN system.

The VESGEN system may be written in any appropriate computer language, such as by way of a non-limiting example, it may be written in Java as a plug-in for the image processing software ImageJ, National Institutes of Health, USA. The VESGEN system as an ImageJ plug-in may make use of many built-in functions and plug-ins distributed with ImageJ, such as for example, skeletonizing and calculating the distance map of the vessel, as well as extensive and reliable input and image manipulation tools. The VESGEN system may be modified for specific applications or as an NIH ImageJ-independent stand-alone code. Moreover, the VESGEN system may be written in any appropriate computer language and/or be compatible with any appropriate computer language. It should be understood that the VESGEN system is not limited to being written in Java as a plug-in for the NIH Image J processing software. It may be written in any appropriate computer language.

Currently blood vessels of the human microvasculature, including arterioles and capillaries, are not capable of being visualized by noninvasive imaging such as MRI and Doppler ultrasound because of insufficient resolution of these clinical imaging modalities. The VESGEN system may be used to analyze such. The VESGEN system may analyze vascular images via a two-dimensional, x-y image matrix that may be black and white, color, grayscale or a combination of such. In the alternative, the VESGEN system may analyze vascular images via a three-dimensional, x-y-z image matrix that may be black and white, color, grayscale or any combination of such.

The VESGEN system may be used to conduct any appropriate analysis. Set forth below are some exemplary embodiments of the analysis that may be conducted using the VESGEN system. These are merely exemplary embodiments and are not intended to be an exhaustive list and the present teachings are not limited to the exemplary embodiments described below. The VESGEN system may be used with any appropriate analysis, quantification, study or the like.

Figure 3:
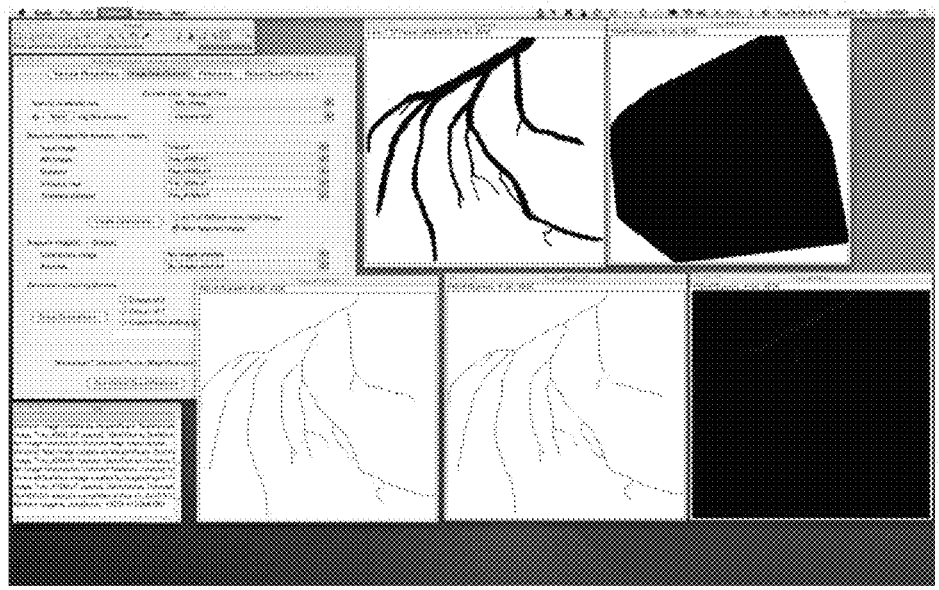
FIG. 3 is an exemplary screen shot of some embodiments of the VESGEN system of images inputted into the VESGEN system.

The VESGEN system may only require user knowledge of image pre-processing to binarize the vessels. The sole user input requirement may be a binary (black/white) digital image in which the vascular architecture (i.e., vascular morphology or pattern) that may appear in black or as otherwise may be appropriate. An exemplary image of such is shown in FIG. 3. An original vascular grayscale or color image acquired by brightfield or fluorescence microscopy may be used and may be pre-processed into the binary input image. An optional user input requirement may be the microscope calibration factor so that the quantified results output may be specified in physical units such as microns in addition to pixels (or voxels).

The VESGEN system may also offer control options from fully automated "one-click" analysis given a primary input, to step-by-step control over each image and algorithm used in an analysis, all within a single user-friendly user interface. Features may be built-in that allow the VESGEN system to readily accommodate new, user-defined algorithms written as Java classes or ImageJ plug-ins and may permit access to C++ methods residing in external libraries, by way of non-limiting examples. The VESGEN system may integrate/cooperate with ImageJ to allow access to any ImageJ process, method, or script. Use of the VESGEN system user interface controls may be interspersed with those of the ImageJ user interface, which may allow modification or correction of intermediate images as appropriate or the study of new, experimental algorithms.

Figure 6:
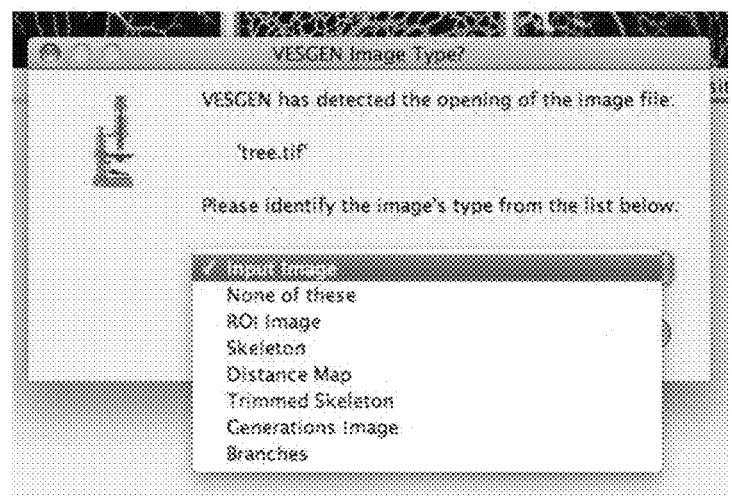
FIG. 6 is an exemplary screen shot showing a step of opening an image in the VESGEN system.

If images opened directly in ImageJ have titles that adhere to the VESGEN system's prescribed format such as "ROI" (region of interest), "SKEL" (skeleton), and "DM" (distance map, the VESGEN system may recognize and assign them to their appropriate role in a given study, analysis, quantification or the like; if not, they may be assigned by user-interactive pop-up dialogue. An exemplary screen shot of such is shown in FIG. 6. If no such intermediate images exist, users may pre-select from among multiple, alternative algorithms to allow the VESGEN system to create the images automatically. The user may also specify which optional steps of an analysis will be performed following initial selection of a vascular morphology option from 1) Vascular Tree, 2) Vascular Network, or 3) Tree-Network Composite, such as that shown in FIG. 3. For example, the user may or may not enter a Microscope Calibration Factor, may or may not combine branching generations into fewer groups, and may or may not select options for generating the ROI. The VESGEN system may provide a simple programmatic interface for users to define custom analysis processes (a "view") by defining all the relationships between a primary binary input, the intermediate image(s) derived from it, the algorithm(s) that can create them, the output(s) that may be produced, and the algorithms to measure them. The algorithms that may be incorporated with the VESGEN system may include a straight Image) plug-in and may therefore also be executable even in the absence of an active VESGEN system user interface session, but are not limited to such.

The VESGEN system may further provide a user interface to both guide and allow control over the users' vascular analysis, study, quantification, or the like process. An option may be provided to select a tissue type—such as by way of a non-limiting example, Tree, Network or Tree-Network Composite—which may determine the general collections of algorithms, intermediate images, and output images and measurements that may be produced by the VESGEN system. The user interface may automatically restructure itself to provide customized user controls for studying the requested type of tissue, as well as specific user-type selected analysis. A user selection such as Vascular Tree type may be linked to a user interface listing the Vascular Tree-dependent analysis options such as type of ROI, Generation Grouping options and Microscope Calibration Factor.

Figure 4:
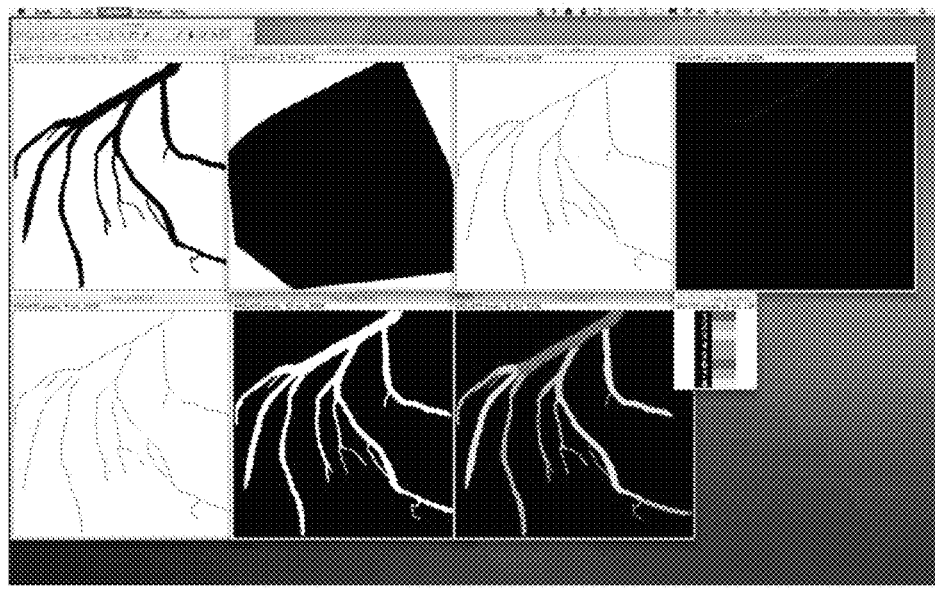
FIG. 4 is an exemplary screen shot of some embodiments of the VESGEN system of output images processed into various vascular maps of branches and generations.
Figure 5:
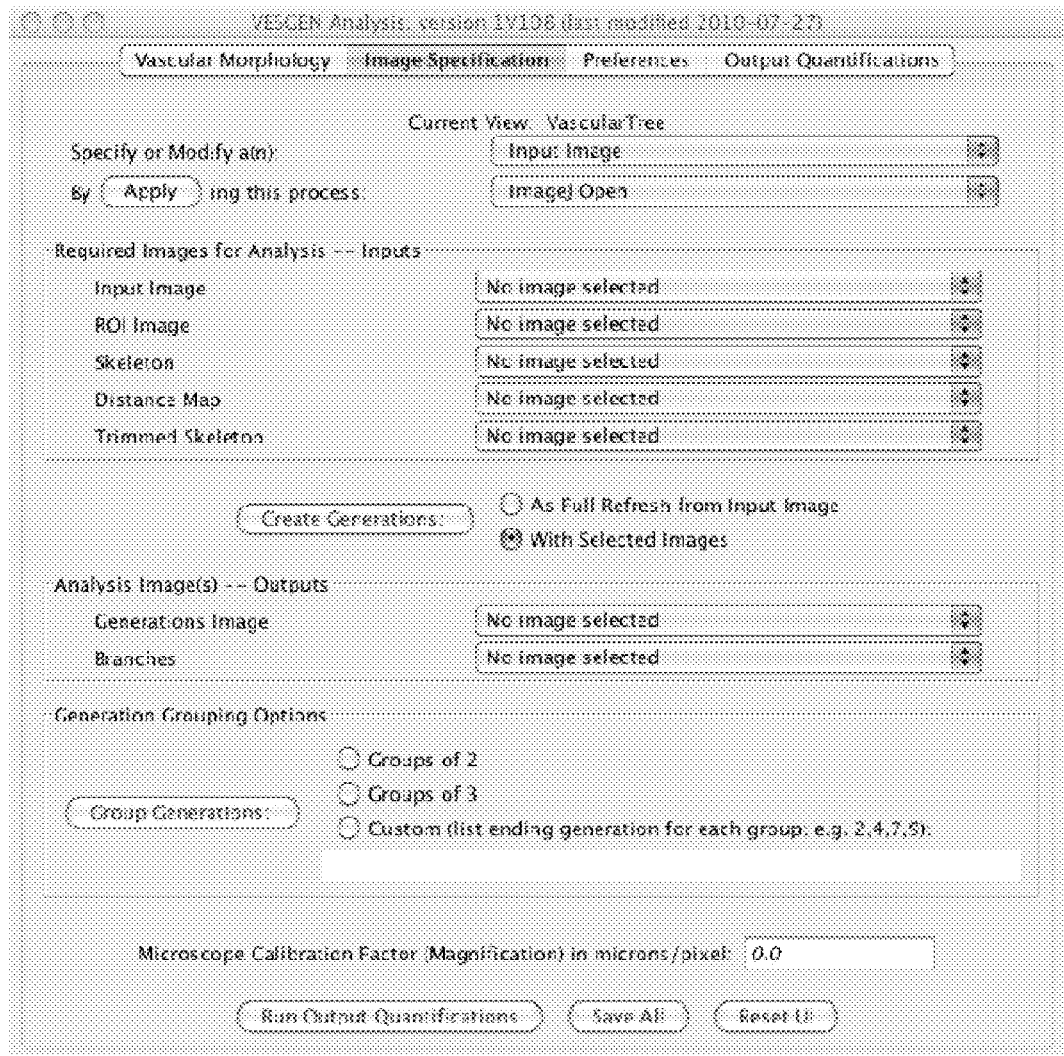
FIG. 5 is an exemplary screen shot of some embodiments of the VESGEN system showing an image specification panel.

More specifically, the VESGEN system may require input of a user provided vascular binary image of an item that is to be analyzed, studied, quantified or the like for which one of the three analysis options may be selected: (1) Vascular Tree; (2) Vascular Network; or (3) Tree-Network Composite, which may determine the general collections of algorithms, intermediate images, and output images and measurements that may be produced. The VESGEN system may then output images processed into various vascular maps, overall image measurements and measurements specified for individual vascular branching generations—an exemplary image of such is shown in FIG. 4. To analyze the input image, the user may select the desired analytical option that may include Vascular Tree, Vascular Network, or Tree-Network Composite from the user interface and may select the desired series of output images, and then further may select custom measurements on the image collection. An exemplary screen shot of the image specification panel is shown in FIG. 5.

Figure 7:
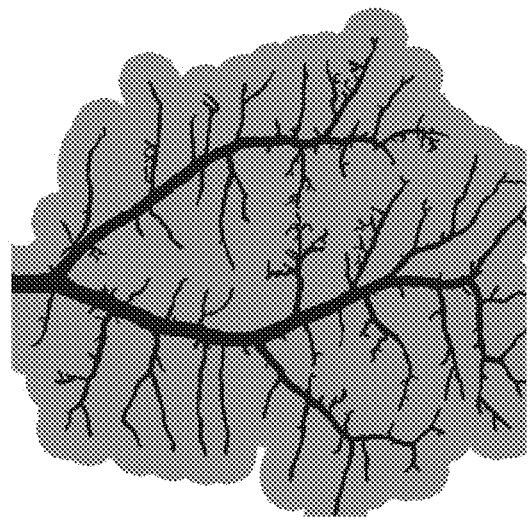
FIG. 7 is an exemplary image from the VESGEN system depicting a threshold map setting the region of interest a fixed distance from a vessel border.
Figure 8:
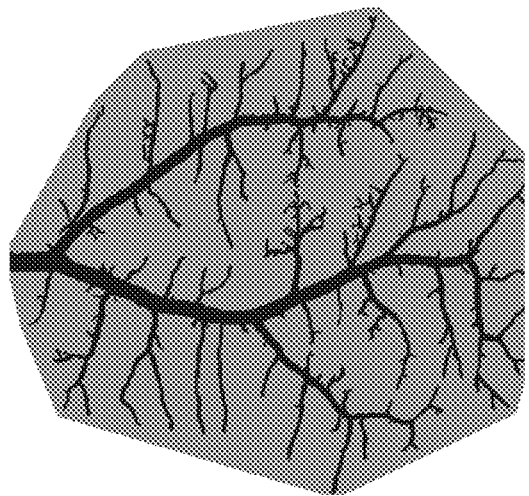
FIG. 8 is an exemplary image from the VESGEN system depicting a convex hull algorithm image that creates a convex hull around a vessel and enlarges it.
Figure 9:
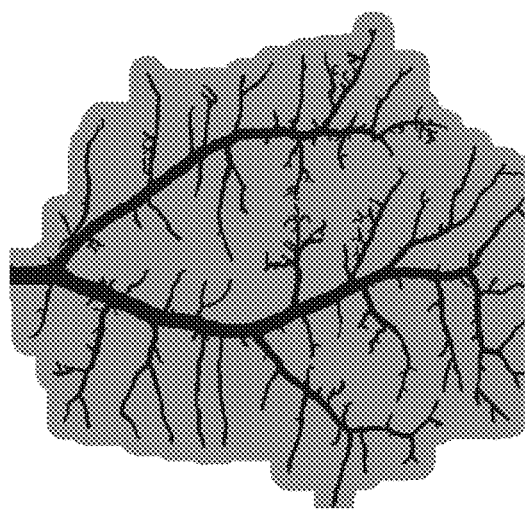
FIG. 9 is an exemplary image from the VESGEN system depicting performance of a dilation of a vessel boundary to determine the region of image.
Figure 10:
FIG. 10 is an exemplary image from the VESGEN system depicting select trees, which may determine a region of interest boundary as halfway between a selected tree(s) and any other non-selected vessel in the image.

Parameters of the user-selected tree, network or composite tree-network option may be reported in pixel or voxel units and optionally in physical units calculated by the system if a microscope calibration factor is provided by the user. Other system options may include saving user preferences and refreshing the analysis. Image processing algorithms may include, but are not limited to such: algorithms for automatic region of interest detection (an exemplary image of such is shown in FIG. 7), skeleton creation, identifying branch point types, and assigning branches to generations. Region of interest algorithms may include a method that may find the midpoint between a selected vessel region and other non-selected vessels, a method that may find a modified convex hull of the vessel (an exemplary image of such is shown in FIG. 8), a method that may use a dilation of the vessel area (an exemplary image of such is shown in FIG. 9), and a method based on the outline size. Algorithms for creating a skeleton may include using the region of interest to correct for artifacts, or using the standard ImageJ method. Algorithms to create the trimmed skeleton may detach skeletons of parent and offspring/offshoot vessels from each other and mark special types of points such as branchpoint, endpoint, and endpoint of a trimmed vessel or a combination. To analyze the successive branching generations of vascular trees, highly specialized algorithms may determine the terminal boundaries of branches, and assign branches to the appropriate branching generation (an exemplary image of such is shown in FIG. 10). By way of a non-limiting example, algorithms may include iterative grouping of vessels into successive branching generations based on physiological principles of dichotomous vessel branching into offspring branching to preserve continuity of blood flow, and numerous smaller offshoot vessels to provide metabolic support throughout tissue. These algorithms may use a distance map to determine the local vessel diameter at every point along the vascular skeleton, information on connectivity of the skeleton, and the type of branch points involved.

The user may interact with the VESGEN system for optimization of the output analysis if desired by the user. By way of a non-limiting example, after a vascular tree has been analyzed and mapped into all generations of vessel branching, the user may re-combine the generational results into specified classes of branching, such as small, medium and large branching generations. The vascular region of interest may be automatically determined by the VESGEN system or may be provided by the user. Output results may include, without limitation, vascular maps illustrating generational assignments for vascular trees, digital maps displaying local vessel diameter, the region of interest used to calculate vessel density parameters and output measurements provided as a summary and detailed measurement document.

The VESGEN system may make use of many functions and plug-ins included in NIH ImageJ, e.g., skeletonizing and calculating the Euclidean distance map of the vessels, as well as basic input and image manipulation tools. A method of trimming the skeleton may be built into the VESGEN system. Using the trimmed skeleton in combination with the distance map information may allow for automatic segmentation of tree-type vessels into generations and also more accurate estimation of vessel diameters. Generation segmentation may be performed by first slicing the vessels at all branch points, then recombining the short sliced regions back into generations, based on their average vessel diameter. The automatic segmentation may be performed to occur primarily in two types of locations: at symmetric (daughter) vessel bifurcations, which may result in approximately a 70% change in vessel diameter between generations, and where smaller vessels branch off from the larger, major vessels.

The 70% criterion for determining a change in generation may be modified by a user-selectable tolerance factor. By way of a non-limiting example, if a 15% tolerance factor is specified, a vessel may be labeled as part of the next smaller generation if its average vessel diameter is anywhere between 55% and 85% of the larger parent vessel diameter. This tolerance introduces cases where a vessel may be categorized in one of two generations. An iterative process may be used to assign the final generation, based on the generation levels of neighboring vessels and the connectivity between them. This approach may favor marking daughter vessels at symmetric bifurcations as smaller generations than the parent and may also reduce the occurrence of small sections of vessels being marked as a larger generation when they are connected to smaller generations on both ends. The VESGEN system may permit the user to select any appropriate tolerance factor or none at all.

Another aspect of the complex, innovative method of segmenting the vessels into generations may use an erosion and dilation approach to successively label larger and larger vessels. However, boundaries between generations do not necessarily occur at branch points, and may occur instead when a default or user-defined option of decrease in vessel diameter becomes the boundary of a new, offspring generation. For this reason, this option may be disabled in the current version of the VESGEN system. If it is enabled, this algorithm may be selected in the user interface in the same manner that other algorithms may be selected.

The VESGEN system may be used to analyze, study and/or quantify a wide variety of items. Set forth below are some exemplary embodiments. However, the VESGEN system is not limited to those exemplary embodiments set forth below. By way of a non-limiting example, the VESGEN system may be used in relation to leaf venation patterns, which may require modifying the vascular tree generational assignments according to vascular plant physiological constraints similar, but different from, the vascular animal physiology supporting multiphase blood flow characterized primarily by a high density of red blood cells. The effects of vascular regulators on plant growth or microgravity on vascular morphology and branching may be tested. The VESGEN system may further be used in the angiogenesis research/clinical field for increased understanding and quantification of the effects of vascular therapeutics and regulators on blood vessel form and function in numerous vascular-dependent diseases such as diabetic retinopathy, cancer, coronary artery disease and diabetes among other items, and on the vascular progression in such diseases, and on vascular remodeling in normal physiology such as embryonic development and wound-healing.

The VESGEN system maps typically five to twelve (or greater) generations of vascular branching typically but not always originating from a single parent vessel. These generations may be tracked and measured for critical vascular parameters that may include vessel diameter, length, density and number, and tortuosity per branching generation. The effects of vascular therapeutics and regulators on vascular morphology and branching tested in the human clinical or laboratory animal experimental studies may be quantified by comparing vascular parameters with control groups. Generation segmentation may be performed first by slicing the vessels at all branch points, then recombining the short sliced regions back into generations, based on their average vessel diameter. This automatic segmentation may be performed to occur primarily in two types of locations: at symmetric vessel bifurcations (into offspring vessels), which result in approximately 70% change in vessel diameter between generations and where much smaller vessels (offshoot vessels) branch off from the larger major vessels. The 70% criterion for determining a change in generation is modifiable by a user-selectable tolerance factor, as noted above.

The VESGEN system may provide a user interface to both guide and allow control over the users' vascular analysis process. An option may be provided to select a tissue type (Tree, Network or Tree-Network Composite), which may determine the general collections of algorithms, intermediate images, and output images and measurements that may be produced from the VESGEN system.

Quantification and vascular mapping by the VESGEN system may be applied to numerous experimental and clinical models in vivo. Some applications may include progression of vascular disease in the human retina from ophthalmic clinical images; effects of angiogenic and lymphangiogenic regulators in an avian chorioallantoic membrane, developing murine retina and development of murine and avian embryonic coronary vessels, GI inflammation from food poisoning, and numerous tumor models in rodents such as occur in pancreatic, other GI, breast, prostate, ovarian and brain cancer, as well as serious reproductive disorders such as placental pre-eclampsia. Results may be presented according to the three VESGEN system user options of Vascular Trees, Vascular Networks, and Vascular Tree-Network Composites.

When the Vascular Tree option is selected, vessel parameters may be measured by the VESGEN system in a region of interest within the vascular image despite the vascular trees being highly branching, asymmetric, non-homogenous, structures comprised of tapering vessels. Options for region of interest may include, without limitation: (1) the entire image, (2) the major vascular tree within the image; or (3) a vascular tree selected by the user. Vascular tree parameters may include vessel diameter, vessel tortuosity, fractal dimension, vessel area density, vessel length density, vessel number density, and vessel branch point density.

For Vascular Tree option, the VESGEN system may use the fundamental image processing concepts of 8-neighbor pixel and 26-neighbor voxel connectivity, skeleton, and distance map to create typically five to twelve (or greater) generations (G1-G5 or G12) of vascular branching often but not always starting from a single parent vessel. These generations may be tracked and measured for critical vascular parameters that may include vessel diameter, length, density and number, and tortuosity per branching generation. Both healthy and pathological vascular remodeling processes such as embryonic development and diseases such as cancer and diabetes, as well as the effects of vascular therapeutics and regulators on vascular morphology and branching tested in human clinical or laboratory animal experimental studies may then be quantified by comparing vascular parameters with control groups. Averaging many parameters of a vascular tree such as vessel diameter or vessel length throughout the entire vascular structure is not a highly meaningful analysis when these parameters vary so greatly throughout a branching vascular tree. Therefore, the VESGEN system may measure many of these parameters according to their site-specific location within the vascular tree.

To accomplish the vessel segmentation (i.e., assignment of branching generations), vessels of the major vascular tree and throughout the entire image may be segmented (decomposed) into successively smaller branching generations according to a proportional decrease of vessel diameter. At a symmetric vessel branching or offspring (daughter) bifurcation, blood flow most efficiently when the diameters of the two offspring vessels are 71% ($1/\sqrt{2}$) of the parent vessel diameter according to principles of multi-phase continuum fluid mechanics, because this branching architecture best preserves the blood flows in a smooth (laminar), non-turbulent state to protect the fragile blood cells, which are present in high concentration. Therefore, vessels may be assigned to the next offspring branching generation when diameters of the offspring vessels are 71% of the parent vessel. This symmetric bifurcational offspring arrangement may dictate the branching architecture of a geometrically perfect branching tree (if symmetric branching angles and length were also included). However, cardiovascular and other biological vascular trees may be more variable in their construction. The VESGEN system may, therefore, assign a vessel to its branching generation by applying a tolerance factor to the 71% rule for relatively symmetric offspring vessel bifurcations as previously discussed.

Another analysis consideration is that the most frequent branching event within a vascular tree is the asymmetric offshoot of a much smaller vessel from a larger vessel, which supports the uniform, efficient delivery of blood throughout the tissue. Because of these smaller asymmetric offshoot vessels, larger vessels taper throughout the tree, although tapering may also support the mechanics of blood flow. Thus occasionally a parent vessel can become an off-spring vessel when its local diameter reaches 71% minus a default or user-defined tolerance factor of the average vessel diameter, so that the offspring vessel generation changes at 56%, by means of system-defined conditional logic programming. This method weighs a dichotomous branching event as a stronger condition than an exact 71% change in vessel diameter. The branching within vascular trees that supports animal (mammalian and avian) blood flow is essentially dichotomous (not trichotomous, for example).

Vascular networks are relatively symmetric, homogenous, non-branching, continuously connected structures characterized by enclosed avascular spaces (i.e., holes or lacunae). Vascular trees often develop from vasculogenic capillary networks, and mature capillaries are typically organized as networks. A basic principle of vascular network analysis is that the fractional areas of network vessels and avascular spaces must sum to one, when normalized by the total region of interest area. The two extremes of thin capillary vessels with large avascular spaces such as in the brain, and thick presinusoidal capillary vessels with small avascular spaces such as in the liver, were contrasted. On selection of the Vascular Network option, the VESGEN system may analyze the vascular binary input image for parameters that include fractal dimension other relevant vascular parameters such as vessel area density, vessel length density, and vessel branch density.

Vascular tree-network composites are structures that are geometrically intermediate between trees and networks and often represent a transitional state of development from an immature network to a more mature tree, or an inflamed or diseased state such as healing wounds, tumors and diabetic microvascular disorders such as diabetic retinopathy and nephropathy. When the Vascular Tree-Network Composites option is selected, vessel parameters may be generated as for the Vascular Trees and Vascular Network options. The VESGEN system may quantify the vascular binary input image for parameters that include overall image results as well as generation-based measurements and avascular spaces measurements.

Applications of the VESGEN system code may include two-dimensional (2D) or 3D vascular images acquired as clinical diagnostic images of the human retina and as experimental studies of normal, healthy vascular remodeling, progressive pathological remodeling, as well as the effects of vascular regulators and therapeutics on vessel remodeling, in the avian chorioallantoic membrane and yolk sac, the rodent retina and ear, and/or other relevant 2D and 3D tissue types. Applications of the VESGEN system may be used for predictive modeling studies of the response of human normal and pathological microvasculature to vascular therapeutics and regulators, and to three-dimensional (3D) vascular trees that are characteristic of organs such as the lung and brain.

The VESGEN system may be used for any of the following as by way of non-limiting examples: remodeling of leaf patterns in response to growth, environmental effects, fertilizers, and pesticides, genetic modifications or environmental factors; vascular images acquired as clinical diagnostic images of the human retina and other human tissues such as the intestine, lungs and brain, and as clinical and experimental images of normal, healthy vascular remodeling, progressive pathological remodeling. In addition, the VESGEN system may be used for experimental studies of the effects of vascular regulators and therapeutics on vessel remodeling in avian chorioallantoic member and yolk sac, the rodent retina and ear and other relevant tissue types; other vascular experimental models such as in laboratory animals, ex vivo vascular models such as aortic ring assay, or even in vivo vascular-mimetic cell culture systems; maps and quantifies major parameters of angiogenesis and lymphangiogenesis in vascular trees and networks; vascular trees in the human retina; vascular networks in the mouse retina; network-tree transitions of embryonic coronary vessels— additional uses may include vascular-dependent human diseases such as diabetes, cancer and coronary vessel disease.

By way of a non-limiting example, the VESGEN system may be used for quantification of normal and pathological microvascular remodeling, and therapeutic and diagnostic efficacy, in 2D and 3D, 4D (dynamic or spatiotemporal), and unlimited numbers of bioinformatic dimensions, microvascular images by NASA- and NIH-funded biomedical researchers and other vascular biomedical researchers for investigating normal and pathological vascular remodeling programs, and therapeutic development in the public domain, and by biotech and pharmaceutical companies for therapeutic development, and potentially with further development and application specialization, for diagnostics in ophthalmology clinics. The VESGEN system may also be useful for the predictive modeling of therapeutic efficacy in microvascular applications for NASA's Digital Astronaut and for NIH's Digital Human.

The VESGEN system analysis may be applied to the human retina, experimental rodent retina, remodeling coronary vessels in numerous experimental animal models, and other biomedical research applications. For example, the VESGEN system may be used to segment blood vessels into appropriate branching generations according to vessel diameter and other vascular parameters for intravital blood flow results produced by particle imaging velocimetry (PIV) analysis, and incorporate bioinformatic dimensions such as cell surface receptor localization and density, and vascular drug uptake or release. The VESGEN system may also support predictive and diagnostic modeling that could be implemented for the new, pioneering NASA and NIH initiatives on the Digital Astronaut and Digital Human, respectively. The 2D VESGEN system software may find useful application to botanical research and agribusiness, because leaves are fundamentally characterized in a 'fingerprint' signature fashion by their branching vascular trees and capillary or vasculogenic networks.

By way of a non-limiting example, one important stimulator of blood vessel growth is basic fibroblast growth factor (bFGF), which stimulates vascular remodeling and vessel growth exclusively by stimulation of the growth of new small vessels of vessel generation G5 and greater. The bFGF did not affect vessel number, density or diameter for larger pre-existing vessels of G1-G4. Conversely, an important inhibitor of blood vessel growth, transforming growth factor beta-1 (TGF-beta1) inhibits vascular remodeling and vessel growth exclusively by inhibition of the growth of new small vessels of vessel generation G5 and greater. TGF-beta1 did not affect vessel number, density or diameter for larger preexisting vessels of G1-G4. The stimulator bFGF and inhibitor TGF-beta1 may be regarded as robust but simple regulators of blood vessel growth, because of their selective regulation of the growth of new small vessels. Other important regulators like vascular endothelial growth factor-165 (VEGF-165), also known as vascular permeability factor (VPF), are more complex in their regulatory activities. VEGF-165/VPF has multimodal effects on blood vessel morphology, including stimulation of the growth of new, small blood vessels, and the induction of vessel leakage, vessel swelling and vessel tortuosity. VEGF-165/VPF also stimulates the growth and swelling of the associated lymphatic vascular system, which expands to accommodate the increased interstitial fluid shifts such as are induced in the upper bodies of astronauts in microgravity, and resulting in recently discovered astronaut health problems such as increased intracranial pressure and retinal/vision damage following long-duration space flight. All healthy and unhealthy (abnormal) fluid shifts in the body are tightly regulated by the small vessels (vascular and lymphatic capillaries) except during trauma such as flesh wounds. The VESGEN system may support analysis of such retinal and brain vascular changes mediating the fluid shifts from images of experimental animals and clinical diagnostic images of humans.

The description of steps above may be accomplished in any order and certain steps may be skipped or additional steps added thereto. Moreover, steps may be accomplished manually, automatically or a combination of such. The descriptions of studies and uses are merely exemplary; the VESGEN system may be used in any appropriate manner to measure, analyze, quantify, study or the like any appropriate vascular structure, vessel, vessel morphology or the like. Further, the application and use of the VESGEN system is not limited to only those uses described herein. The VESGEN system may be used to measure, analyze, quantify, study or the like any appropriate item, such as the branching of arterial river systems or complex extraterrestrial life forms.

Additional embodiments and exemplary uses of the VESGEN system according to the present teachings are described below. In the descriptions, all of the details and components may not be fully described or shown. Rather, some of the features or components are described and, in some instances, differences with the above-described embodiments may be pointed out. Moreover, it should be appreciated that these additional embodiments may include elements or components utilized in the above-described embodiments although not shown or described. Thus, the descriptions of these additional embodiments are merely exemplary and not all-inclusive nor exclusive. Moreover, it should be appreciated that the features, components, elements and functionalities of the various embodiments may be combined or altered to achieve a desired VESGEN system without departing from the spirit and scope of the present teachings.

The following are exemplary embodiments and uses of the VESGEN system. The descriptions are for exemplary purposes and the VESGEN system is not limited to that shown and described.

Vascular dropout and angiogenesis are hallmarks of the progression of diabetic retinopathy. However, current evaluation of diabetic retinopathy relies on grading of secondary, indirect vascular effects of disease progression, such as microaneurysms and hemorrhages, by clinical examination instead of by evaluation of actual, primary, directly causative vascular changes. The purpose of this study was to map and quantify vascular changes during progression of diabetic retinopathy by the VESGEN system. Purposes of the study were twofold: 1) to better understand and consequently improve therapeutic treatment of diabetic retinopathy (the major cause of blindness in working-aged adults) and 2) to use this important disease as the paradigm human clinical study to develop and demonstrate the novel, innovative usefulness of the VESGEN system for characterizing other diseases with a strong vascular component such as cancer, heart disease, and other diabetic microvascular pathologies.

In this prospective cross-sectional study, fifteen eyes with diabetic retinopathy were evaluated with fluorescein angiography and color fundus photography, and were graded using modified Early Treatment Diabetic Retinopathy Study ("ETDRS") criteria. Fluorescein angiography images were separated by semiautomatic image processing into arterial and venous trees. Vessel length density (Lv), number density (Nv), and diameter (Dv) were analyzed automatically with the VESGEN system. Each vascular tree may be automatically segmented into branching generations (G1 . . . G8 or G9) by vessel diameter and branching. Vascular remodeling status (VRS) for Nv and Lv was graded 1 to 4 for increasing severity of vascular change in a masked fashion by an experienced vitro-retinal surgeon.

By Nv and Lv, VRS correlated significantly with the independent clinical diagnosis of mild to proliferative diabetic retinopathy (13/15 eyes; the remaining two eyes were more effectively diagnosed by the VESGEN system than by ETDRS, the current prevailing diagnosis system that grades primarily the indirect vascular effects such as density of microaneurysms and hemorrhagic leakage). Nv and Lv of smaller vessels (G≥6) increased from VRS1 to VRS2 by 2.4× and 1.6×, decreased from VRS2 to VRS3 by 0.4× and 0.6×, and increased from VRS3 to VRS4 by 1.7× and 1.5× (P<0.01). Throughout diabetic retinopathy progression, the density of larger vessels (G1-5) remained essentially unchanged, and Dv1-5 increased slightly. The discovery by the VESGEN system of the regeneration capacity of the diabetic retina at VRS2, which corresponds to the ETDRS moderate stage of non-proliferative diabetic retinopathy, is an important discovery acknowledged by new research funding by the National Institutes of Health representing a potential paradigm shift in the understanding and potentially regenerative and reversible treatment of this blinding and vision-impairing disease, which currently is treated only at the late, potentially blinding stage. Such a paradigm shift may occur when this pioneering study is validated by more extensive clinical trials using the VESGEN system.

Vessel density oscillated with the progression of diabetic retinopathy. Alternating phases of angiogenesis/neovascularization and vascular dropout were dominated first by remodeling of arteries and subsequently by veins.

Diabetic retinopathy is one of the leading causes of visual loss among working-aged adults in the United States. The diagnosis and management of diabetic retinopathy may be based on grading of features obtained from clinical examination. Although progression of diabetic retinopathy results from adverse vascular remodeling that includes vascular dropout, ischemia, and finally neovascularization, current diagnosis relies on the grading of secondary vascular effects, such as microaneurysms, leakage, and exudates. It is challenging to directly evaluate changes in retinal blood vessels because of the morphologic complexity of the overlapping, highly branching arterial and venous trees within the human retina.

To study vascular remodeling directly, the VESGEN system may be utilized to map and quantify arterial and venous trees extracted from clinical images obtained by fluorescein angiography and other ophthalmic imaging modalities. The VESGEN system may analyze major vascular branching parameters in a binary (black/white) image of a vascular tree, vascular network, and/or tree-network composite. Mapping and quantification by the VESGEN system may automatically segment vessels within a tree into branching generations (G1, G2, . . . Gx) according to coordinate change in vessel diameter and branching. The VESGEN system may map and quantify vascular trees and networks in the human retina, transgenic mouse retina, and chorioallantoic membrane, an avian model of angiogenesis and lymphangiogenesis. In a non-limiting example, coronary vessel development may be analyzed as an immature vasculogenic network, a transitional network-tree composite, and a mature tapering vascular tree and is described in more detail below. While the descriptions below are exemplary embodiments of the VESGEN system and capabilities of the VESGEN system, the present teachings are not limited to these descriptions and uses. The VESGEN system may be used in any appropriate manner.

To develop the VESGEN system mapping capabilities, proangiogenesis and antiangiogenesis factors were first studied in the avian chorioallantoic membrane, a well-established, experimentally convenient 2D, optically accessible model of microvascular remodeling, angiogenesis and angiogenesis therapeutics. Using the VESGEN system basic fibroblast growth factor (bFGF) stimulated specifically the robust growth of many small vessels. Vascular endothelial growth factor (VEGF)-A, another major angiogenesis regulator, however, had a more complex effect. At low concentrations, VEGF stimulated the growth of new small vessels in a manner resembling stimulation by bFGF. At high concentrations, regulation by VEGF resulted in a more pathological regulatory phenotype, in which the diameter of larger vessels was significantly dilated (accompanied by vascular leakage). Inhibition of angiogenesis by transforming growth factor (TGF) β-1 retained a normal vascular morphology, whereas inhibition by angiostatin rendered the vascular tree highly abnormal and irregular. The steroid drug triamcinolone acetonide (TA) also inhibited the growth of small vessels and, furthermore, thinned the diameters of all vessels throughout the vascular tree except those of the smallest vessels.

Using fractal analysis, one analytical capability of the VESGEN system, vascular morphology in the retinas of patients with normal eyes and those with mild non-proliferative diabetic retinopathy has previously been analyzed. This showed that compared with the normal retina, the combined density of arteries and veins in the non-proliferative diabetic retinopathy retina decreased in the macula but was unchanged in peripheral regions. In the present study of progressive vascular remodeling during diabetic retinopathy, the VESGEN system may be capable of mapping and quantifying branching characteristics of separated arterial and venous trees to reveal generation-specific changes of oscillating vessel density.

Consecutive patients were prospectively enrolled in a cross-sectional study if they met the following inclusion criteria: age older than 18 years, clinical evidence of mild or greater non-proliferative diabetic retinopathy based on dilated fundus examination by an experienced retina specialist, ability to give written informed consent, and no contraindication to fluorescein imaging. All patients were imaged by experienced retinal photographers with color fundus photographs and 50° fluorescein angiography. Color fundus photographs were graded and ranked, in a masked fashion by the retina specialist, in order of increasing severity of retinopathy with the use of a modified ETDRS protocol.

Angiography was performed by injection of fluorescein into the vasculature, followed by fluorescence imaging of progressive filling of the retinal vasculature. Fluorescein angiography images were saved as digital grayscale images (2392×2048 pixels). The peak transit images of the fluorescein angiography image were graded in a masked fashion by the retina specialist. Given the highly detailed image analysis capabilities of the VESGEN system, only fluorescein angiograms judged to be of excellent image qualities were selected based on resolution of the critically important smaller vessels. Only one fluorescein angiography was excluded from analysis based on image-processing grounds because of insufficient resolution of small vessels at higher zoom ratios. Fluorescein angiography images were also graded in a masked fashion by the retina specialist and were placed in order of increasing disease progression based on the severity of ischemia and the status of capillary perfusion in the foveal avascular zone.

In some exemplary embodiments of the study, thirteen eyes from twelve patients were independently graded using the ETDRS criteria as two with mild non-proliferative diabetic retinopathy, five with moderate non-proliferative diabetic retinopathy, five with severe non-proliferative diabetic retinopathy, and one with early proliferative diabetic retinopathy ("PDR"). To obtain a minimum statistical sampling of n=3 for each analysis group as classified by vascular remodeling status, two additional fluorescein angiography images (one mild non-proliferative diabetic retinopathy and one PDR) were included for a total of fifteen study eyes. The ranking of eyes in order of increasing severity of diabetic retinopathy was performed in a masked, independent fashion by the retina specialist after the VESGEN system analyzed all fifteen images.

Images acquired at the stage of full arteriovenous filling were selected for analysis by the VESGEN system because the goal was to analyze both arterial and venous trees. The original fluorescein angiography grayscale images (2392× 2048 pixels) were processed into binary images using appropriately sized (large cinema-style) monitors at several zoom ratios, affording almost one-to-one pixel correspondence. Within each fluorescein angiography image, a vascular pattern of overlapping arterial and venous trees was extracted by semiautomatic computer processing, as described previously, now using an appropriate image editing software because of the layering and opacity capabilities. The grayscale fluorescein angiography image may first be inverted so that the blood vessels appeared dark. Image contrast was optimized to obtain sufficient contrast of small vessels by the brightness/contrast tool. A duplicate of the contrast-enhanced image may be transformed to a binary image with the thresholding tool to sufficiently retain larger vessels and some small vessels. Final selection of vessel morphology may be accomplished by placing this image above the contrast-enhanced layer and, to maximize visibility of both layers, converting vessels from black to red at a reduced opacity and deleting the white background. The pencil and eraser tools may be used to define vessel edges and erase some areas of red background. The red image may be converted to black vessels and white background with the magic wand and fill tools, thereby yielding the final binary (black/white) vascular pattern.

The vascular pattern may be separated into arterial and venous trees according to comparison with earlier and later images in the fluorescein angiography series to identify various stages of arteriovenous filling of injected fluorescein dye by which arteries are filled before veins. This may include characteristic arterial and venous morphology; reference to the color fundus images in which arteries are redder and veins more purple; and basic principles of vascular tree connectivity, branching, and tapering. By way of a non-limiting example, arterial and venous trees tend to originate from the optic disc in pairs. Arterial vessels are of smaller diameter than venous vessels and are often more tortuous. The VESGEN system may analyze two-dimensional images of vascular pattern. Therefore, vessels originating at the optic disc may be cut off where they appeared to bend out of the x-y image plane into the z-plane of the optic nerve. Small vessels supplying only the immediate region of the optic nerve may also be excluded. Once a vascular tree was identified as arterial or venous, the tree may be followed from its origin to its termination at the smallest generations according to vessel connectivity, bifurcational branching, and tapering (morphologic characteristics of a mature vascular tree). Vessels that appeared to be non-patent (i.e., without blood flow) because of occlusion, remodeling, or location within hemorrhagic regions may be excluded from the binary vascular pattern. In these embodiments, vessel interpretation may be decided by agreement between two experienced image processors, subject to final decision by the senior processor. Although, vessel interpretation may be accomplished in any appropriate manner.

Figure 11:
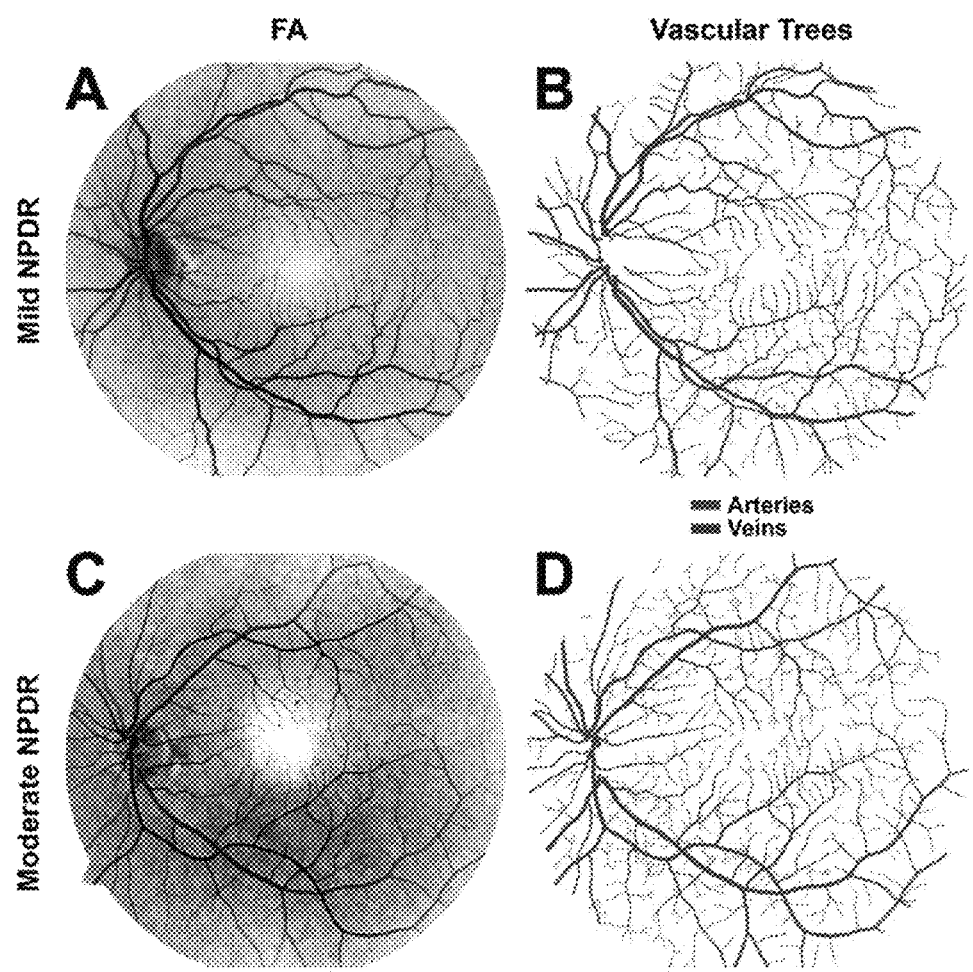
FIG. 11 are exemplary fluorescein angiography images of an eye converted into binary images of vascular pattern for mapping and quantification of vascular trees using some embodiments of the VESGEN system.
Figure 12:
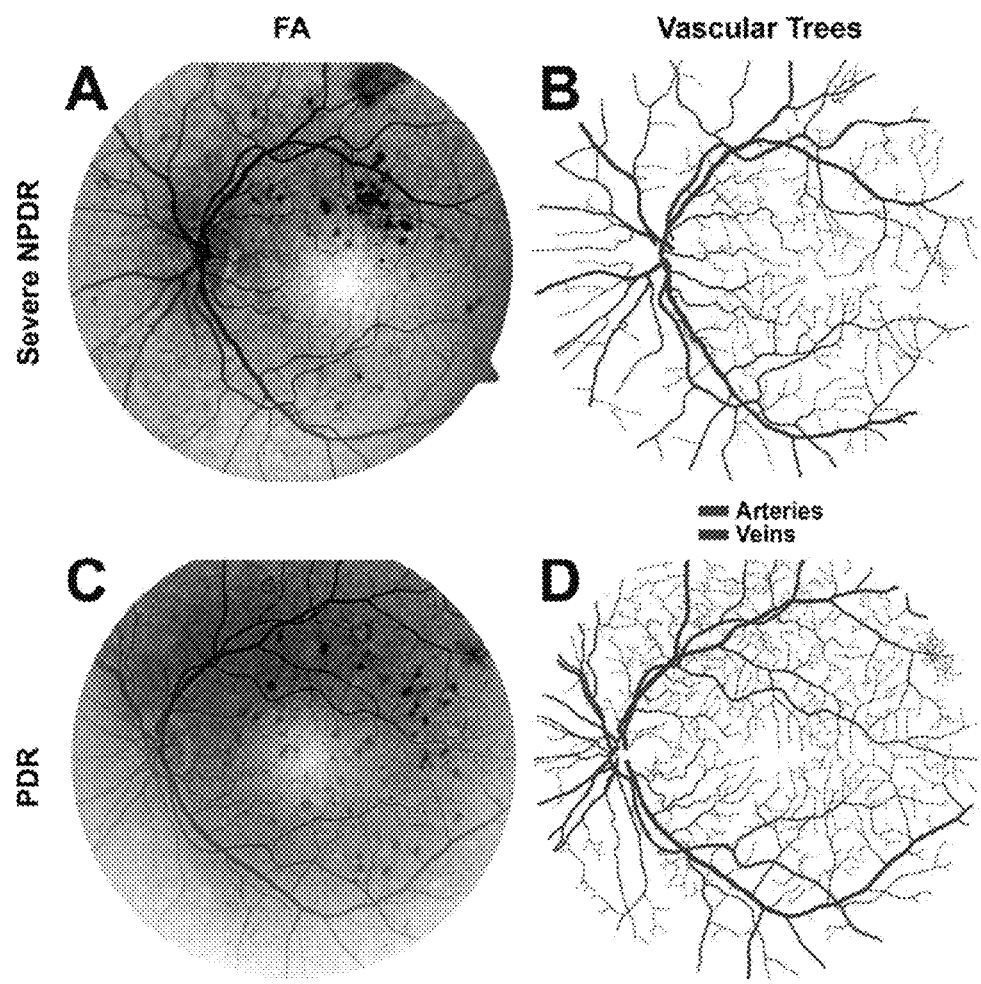
FIG. 12 are exemplary fluorescein angiography images of an eye converted into binary images of vascular pattern for mapping and quantification of vascular trees using some embodiments of the VESGEN system.

The VESGEN system may only need an input of a binary (black/white) image of vascular pattern for mapping and quantification of vascular trees, networks, or tree-network composites, an example of which is shown in FIG. 11. For measurement of density-based parameters, the VESGEN system may import a user-supplied image defining the region of interest (an example of which may be shown by the black circular regions of FIGS. 13 and 14).

Output parameters generated by the VESGEN system may include, without limitation, vessel number density (Nv), vessel length density (Lv), vessel area density (Av), vessel branch point density (Brv), vessel tortuosity (Tv), fractal dimension (Df), and vessel diameter (Dv) for branching generations G1, G2, Gx. By way of non-limiting example, Dv1-5 denotes Dv with respect to branching generations G1-G5. Skeletonized (linearized) mappings may be used to quantify Nv, Lv, and Brv in association with distance maps and other specialized mappings. The skeleton may be a linearized map of vessel connectivity in which diameters of vessels may be reduced to the width of a single pixel. By comparing morphologic characteristics of the input vascular pattern image and its skeleton image as the first mapping output, the VESGEN system may map the vessel generations (G1-G9 for this study; see FIGS. 13 and 14) and then may quantify vessel density parameters such as Lv and Nv by referring to the region of interest input image. A trimmed skeleton may exclude linear elements of vessel skeletons lying within the diameters of adjacent vessels, thereby providing precise measurements of Lv and Dv for specific branching generations such as Lvl. Density functions such as Nv, Lv, Av, and Brv may be obtained by normalization to the surface area of the region of interest (see FIGS. 13 and 14).

Further, vessel branching generations (G1-Gx) may be determined by the VESGEN system according to relative decreases in vessel diameter. Blood flow velocity may be conserved at a symmetric vessel bifurcation, where the diameter of a symmetric offspring vessel decreases to 71% ($1/\sqrt{2}$) of the diameter of the parent vessel. A decrease of vessel diameter to 71% may, therefore, be used as the primary determinant of a new branching generation. However, as seen in biological branching trees (FIGS. 11-14), the branching of relatively symmetric offspring vessels may not be perfectly symmetric; the diameters of very few offspring vessels are of the 71% ideal value, and vessels almost invariably taper. To accommodate a reasonable range of vessel diameters within a biological (nonmathematical) branching generation, the VESGEN system may contain an appropriate tolerance factor, such as by way of a non-limiting example, a 15% default tolerance factor that may be user-adjustable. The 15% default value was used in this exemplary study. The most frequent branching event in a vascular tree is generally the asymmetric offshoot branching of a much smaller vessel from a larger vessel, presumably because of space-filling requirements of the tissue for vascular branching.

A preliminary grouping study of arterial vessel density using two images of sparse vessels (severe non-proliferative diabetic retinopathy) and two images of dense vessels (moderate non-proliferative diabetic retinopathy) may be performed with the VESGEN system. Results showed that the grouping of large (G1-G3) and medium (G4-G5) vessels together as (G1-G5) and a second grouping of all small vessel generations as G≥6 were generally optimal for quantifying where remodeling events fundamentally differed within the branching tree. As described in below, vascular remodeling status (VRS) was obtained from the VESGEN system results for vessel density by Nv and Lv compared with the progressive clinical ranking of the fifteen eyes by increasing severity of diabetic retinopathy. Four stages of vascular remodeling status may be identified from the Nv and Lv results for the mild non-proliferative diabetic retinopathy to the very severe non-proliferative diabetic retinopathy/PDR images and may be labeled VRS1 to VRS4 to correspond with increasing severity of diabetic retinopathy. Presentation of the results, therefore, distinguishes among mild non-proliferative diabetic retinopathy, moderate non-proliferative diabetic retinopathy, severe non-proliferative diabetic retinopathy, and very severe non-proliferative diabetic retinopathy/PDR, as determined by ETDRS clinical diagnosis, and vascular remodeling status VRS1 to VRS4, as may be determined by the analysis using the VESGEN system.

Variation may be assessed by calculating the mean±SE (equal to SD divided by the square root of sample number) and by P values from a Student's t-test of equal variance ($\alpha=0.05$). A one-tailed test estimated whether expected decreases or increases between groups were significant; a two-tailed test estimated confidence in overall differences (whether increased or decreased).

Vessel density oscillated with progression from mild non-proliferative diabetic retinopathy to very severe non-proliferative diabetic retinopathy/early PDR by alternately displaying angiogenesis and vascular dropout phenotypes, as may be mapped and quantified by the VESGEN system. Using visual inspection, the vessel density of both arterial and venous trees appeared to increase significantly from mild to moderate non-proliferative diabetic retinopathy, decrease from moderate to severe non-proliferative diabetic retinopathy, and increase again from severe to very severe non-proliferative diabetic retinopathy/early PDR (see FIGS. 11-14). This alternation or oscillation may be observed in the vascular patterns extracted from the fluorescein angiography images (see FIGS. 11 and 12) but may be clearly more apparent in the maps of generational branching from the VESGEN system (see FIGS. 13 and 14).

Arterial and venous trees extracted from fluorescein angiography images of retinas diagnosed as having mild non-proliferative diabetic retinopathy (A) and moderate non-proliferative diabetic retinopathy (C) may be displayed as overlapping vascular patterns (B, D). Although the trees may be shown in red and blue for illustration, the image of a single isolated tree is imported into the VESGEN system as a binary (black/white) image. To preserve visualization of the critically important small blood vessels, the images may be presented in two figures (see FIG. 12 for later stages of diabetic retinopathy). The fluorescein angiography images of FIGS. 11 and 12 were selected as illustrations because their results from the VESGEN system and clinical ranking are median values for their groups (and close to mean values of vascular density by Nv and Lv; see FIGS. 15 and 16).

Arterial and venous trees extracted from fluorescein angiography images of retinas diagnosed as having severe non-proliferative diabetic retinopathy (A) and PDR (C) may be displayed as overlapping vascular patterns (B, D). As for FIG. 11, the fluorescein angiography images were selected because the results from the VESGEN system and clinical rankings are median values (see FIGS. 15 and 16).

Figure 13:
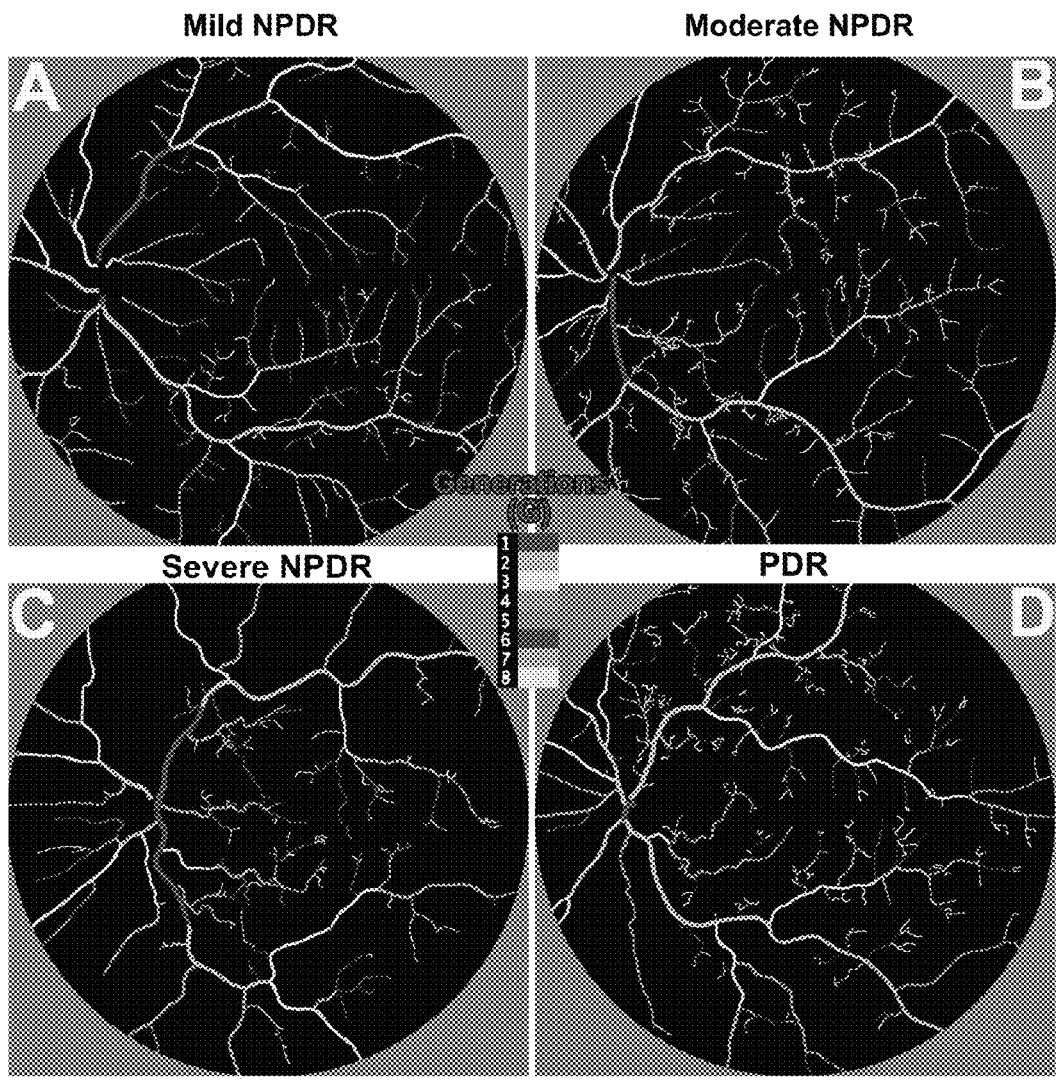
FIG. 13 are exemplary images of branching generations mapped within arterial patterns of an eye by some embodiments of the VESGEN system.

Eight branching generations (G1-G8) were mapped within arterial patterns by the VESGEN system (FIG. 13). Vessel density increased from mild non-proliferative diabetic retinopathy (A) to moderate non-proliferative diabetic retinopathy (B), decreased at severe non-proliferative diabetic retinopathy (C), and increased again at PDR (D) stages of diabetic retinopathy. The arterial maps, therefore, display an oscillation between the opposing vascular phenotypes of angiogenesis (or neovascularization) and vascular dropout. Imaging fields for the fluorescein angiography images vary slightly with each photograph, but normalizing vessel density parameters by the region of interest corrects for this small variation. In these illustrations, diameters of smaller vessels (G≥4) were enlarged by two pixels to increase visibility.

Figure 14:
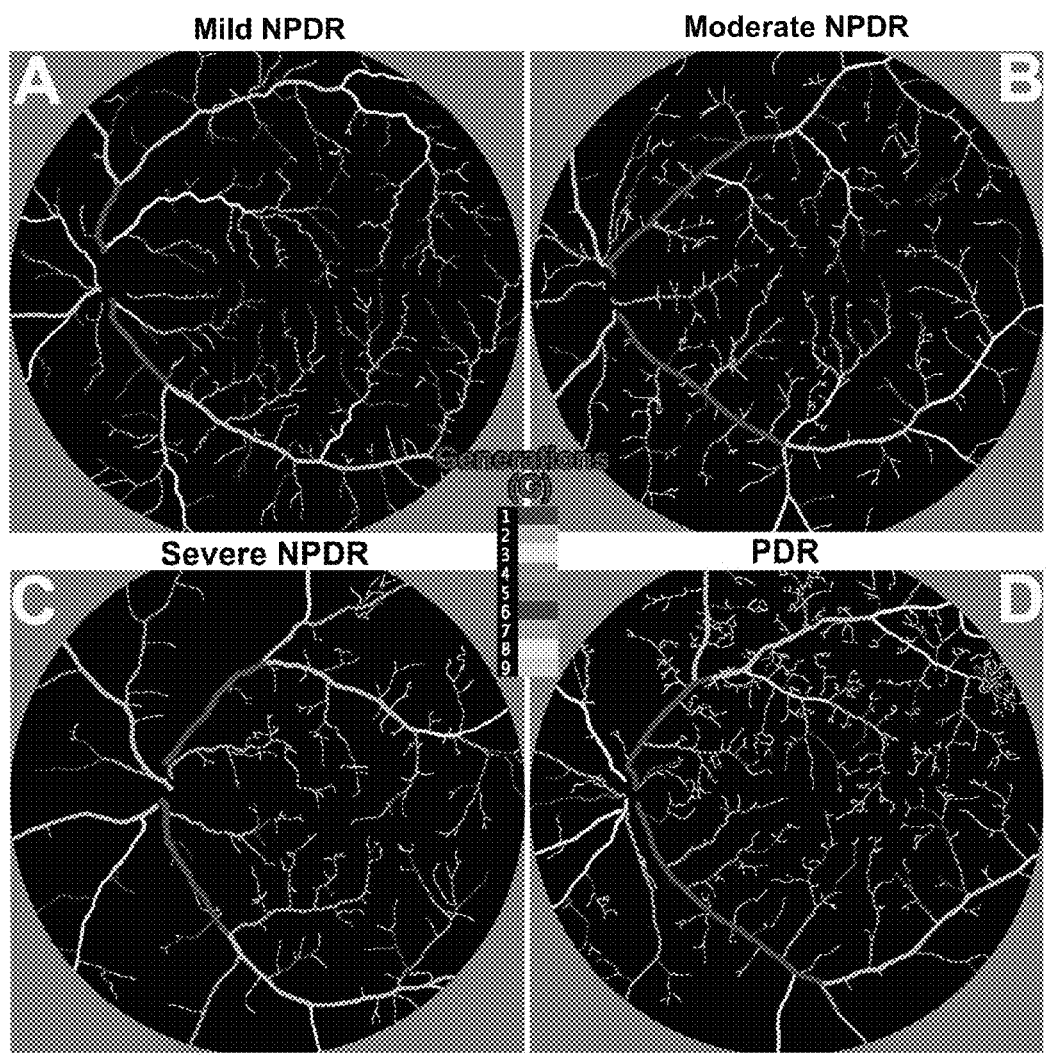
FIG. 14 are exemplary images of branching generations mapped within venous patterns of an eye by some embodiments of the VESGEN system.

Oscillation of venous density. Eight or nine branching generations (G1-G8 or G9) were mapped within venous patterns by the VESGEN system (FIG. 14). Vessel density increased from mild non-proliferative diabetic retinopathy (A) to moderate non-proliferative diabetic retinopathy (B), decreased at severe non-proliferative diabetic retinopathy (C), and again increased at PDR (D) stages of DR. Venous maps appear to correlate positively with results for arterial maps (FIG. 13). The diameters of small veins (G≥4) were enlarged by two pixels for improved visibility.

Figure 15:
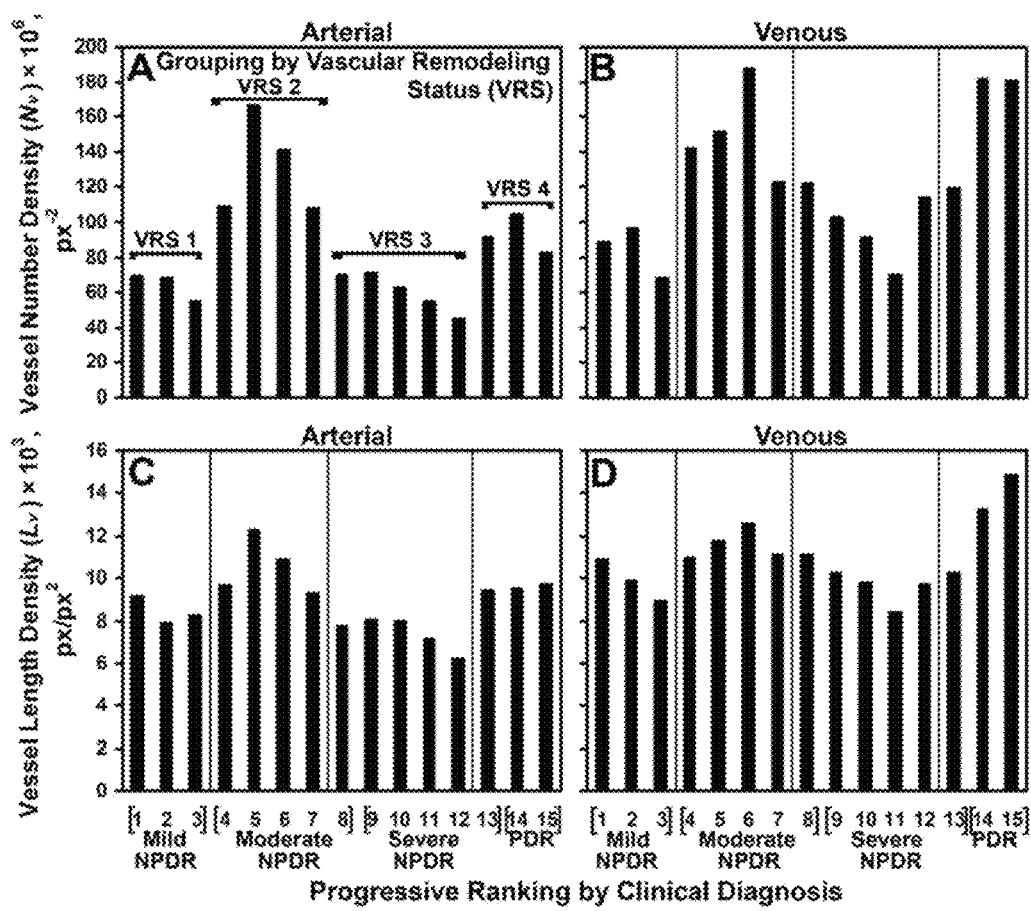
FIG. 15 are graphical representations of grouping of vascular remodeling status by ranking of clinical diagnosis and VESGEN system results of density of vessels.

Progression of vascular remodeling as measured by Nv and Lv for all vessels within an arterial or a venous tree image correlated significantly, but not absolutely, with ranked progression by clinical diagnosis (13/15 eyes; FIG. 15). Nv and Lv generally confirm each other as indicators of the space-filling capacity of a branching tree. Grouping by arterial results for Nv (FIG. 15A) was particularly clear and provided the primary basis for defining the VRS as VRS1 to VRS4, corresponding to increasing severity of diabetic retinopathy (confirmed by all other results; FIG. 15). In particular, the VRS groups of 1, 2, 3, and 4, as defined by Nv and Lv, correlate positively with ETDRS diagnoses of mild non-proliferative diabetic retinopathy, moderate non-proliferative diabetic retinopathy, severe non-proliferative diabetic retinopathy, and very severe non-proliferative diabetic retinopathy/PDR. Significantly, two arterial trees that ranked highest in the clinically diagnosed groups of moderate non-proliferative diabetic retinopathy and severe non-proliferative diabetic retinopathy were clearly reclassified by arterial remodeling status (FIG. 15A) as VRS3 (eye 8) and VRS4 (eye 13). Vascular changes for reclassification by the VESGEN analysis into a more advanced stage are more apparent at an earlier clinical stage of diabetic retinopathy in arterial trees than in venous trees, for both Nv and Lv than by ETDRS (FIG. 15). Nonetheless, the ranked clinical diagnosis based on secondary vascular features provided a necessary first-round sorting or binning of disease progression, before subsequent grouping by vascular remodeling status, as determined by Nv and Lv. Grading of the vascular remodeling status by Nv or Lv may be helpful for improved, predictive diagnosis and treatment but may not be sufficient to grade DR progression because of the non-uniqueness of groups (i.e., vessel density of VRS1 resembles that of VRS3, and vessel density of VRS2 resembles that of VRS4).

To determine appropriate analysis groups of progressive vascular remodeling for subsequent quantification by the VESGEN system, the fluorescein angiography images may be ranked by clinical diagnosis from 1 to 15, in order of increasing severity of diabetic retinopathy. Diagnosis may be based on modified ETDRS clinical criteria that may include density and location of microaneurysms, hemorrhagic leakage, exudates, ischemic areas, neovascularization, and vascular arcades. The density of all vessels (overall density) determined by the VESGEN system may be plotted and compared with clinical ranking. Vessel number density (Nv) and vessel length density (Lv) may be appropriate measures of the space-filling capacity of tree-branching patterns. Results reveal oscillation between angiogenesis and vascular dropout as a direct, positive function of clinically diagnosed progression of diabetic retinopathy. The plots show agreement for these oscillatory trends between arterial and venous trees and between Nv and Lv. According to arterial results for Nv (A), the highest-ranking patients for the clinically diagnosed moderate and severe groups (eyes 8 and 13) were reclassified by vascular remodeling status as VRS3 (correlated to severe non-proliferative diabetic retinopathy) and VRS4 (correlated to very severe non-proliferative diabetic retinopathy/PDR). Because of the clear binning of clinically ranked grading and dominance of arterial remodeling compared with venous remodeling during the first angiogenic phase (mild to moderate), arterial results for Nv were used to define the four analysis groups, VRS1 to VRS4. Black vertical lines indicate this grouping of arterial and venous trees by vascular remodeling status into VRS1 to VRS4.

Figure 16:
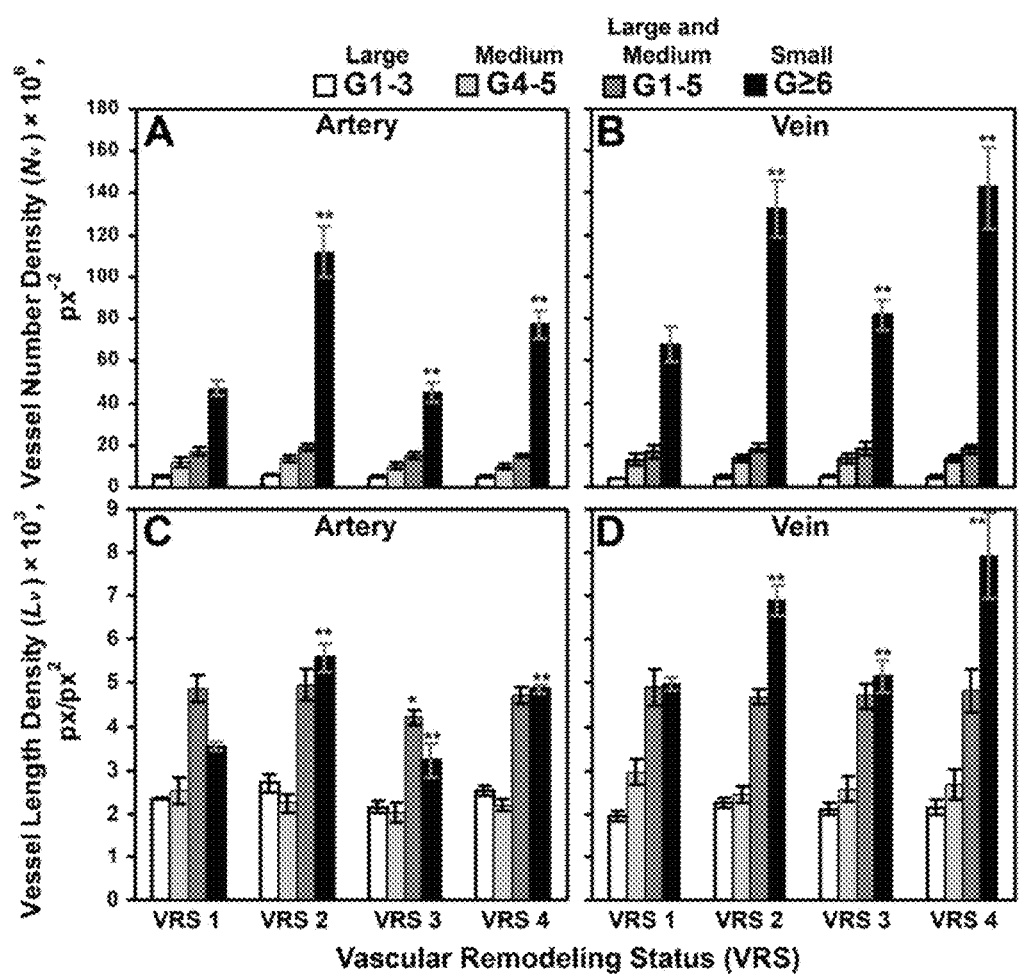
FIG. 16 are graphical representations of results grouped by vascular remodeling status of arteries and veins from the VESGEN system.

Referring now to FIG. 16, there are shown graphical representations of results grouped by vascular remodeling status of arteries and veins from the VESGEN system that represent an updated, more sensitive predictive measurement of vascular status for progression of diabetic retinopathy than established ophthalmic ETDRS criteria. When grouped by vascular remodeling status (FIG. 16), the density of smaller vessels (G≥6) by Nv and Lv increased up to 2.4× from VRS1 to VRS2, decreased by as much as 0.4× from VRS2 to VRS3, and increased up to 1.74× from VRS3 to VRS4 (all for Nv, P<0.01). The density of larger vessels (G1-5) did not change significantly during vascular remodeling (all P 0.05 by two-tailed t-test; FIG. 16). Hence, by correlation of vascular remodeling status with ranked clinical diagnosis, diabetic retinopathy appeared to progress by net angiogenesis from mild to moderate non-proliferative diabetic retinopathy, by net vascular dropout from moderate to severe non-proliferative diabetic retinopathy, and by net angiogenesis/neovascularization from severe to very severe non-proliferative diabetic retinopathy/early PDR (FIGS. 11-14).

Using the analysis from the VESGEN system, angiogenesis and vascular dropout oscillate with progressive vascular remodeling of smaller arteries and veins. By Nv and Lv, the oscillation between angiogenesis and vascular dropout during diabetic retinopathy were restricted to smaller blood vessels (G≥6), as quantified by changes in vessel density during progression of vascular remodeling status from VRS1 to VRS4. Relative increases in vessel density by Nv and Lv were greater for arteries than for veins in the first phase of angiogenesis (VRS1-VRS2) but greater for veins in the second phase of angiogenesis (VRS3-VRS4). Data is plotted as mean±SE. *P≤0.05 and **P≤0.01, one-tailed t-test, for confidence estimation of either increased or decreased vessel density for G1-5 and G≥6 from VRS1 to VRS2, VRS2 to VRS3, and VRS3 to VRS4. By a two-tailed t-test (for estimation of confidence in differences), P-values of Nv≥6 and Lv≥6 for all arterial and venous transitions were ≤0.01, except arterial and venous Lv≥6 for VRS3 to VRS4, which were 0.02.

Figure 17:
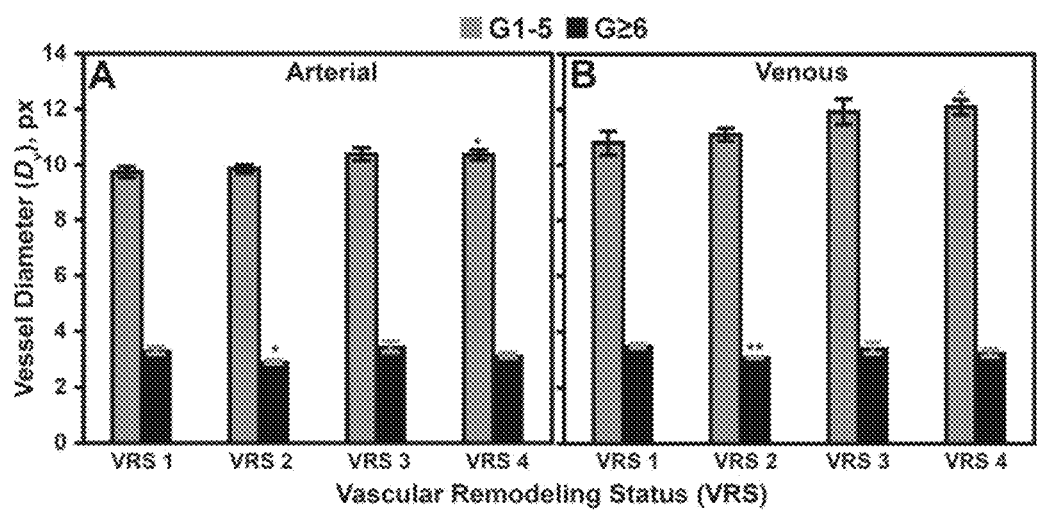
FIG. 17 are graphical representations of vessel diameter of medium sized vessels (arterial and venous) of vascular remodeling status from the VESGEN system.

Referring now to FIG. 17, there are shown graphical representations of vessel diameter of medium sized vessels (arterial and venous) of vascular remodeling status from the VESGEN system that represent an updated, more sensitive predictive measurement of vascular status for progression of diabetic retinopathy than established ophthalmic ETDRS criteria. Increases in the diameters of larger arteries and veins (Dv1-5) appeared to be small but consistent throughout the progression of diabetic retinopathy (FIG. 17). For smaller vessels, Dv≥6 was relatively constant, at least at this level of image resolution, whereas smaller vessels measured only several pixels in diameter. Vessel area density (Av) measured the coupled effects of space-filling branching (Lv) and vessel width (Dv) because it was directly proportional to Lv·Dv. Therefore, results for Av (not shown) in this study were not particularly helpful given the contrasting trends for Lv and Dv.

Using the analysis from the VESGEN system, the diameters of large and medium-sized vessels were shown to increase with progressive vascular remodeling. By measurements of Dv, the diameters of large and medium-sized arteries and veins (G1-5) increased slightly, but consistently, with progressive vascular remodeling. The diameters of smaller vessels did not appear to vary greatly with disease progression. Data are plotted as mean±SE. *P≤0.05 and **P≤0.01, one-tailed t-test, for confidence estimation of increased diameter during vascular remodeling of VRS2, VRS3, and VRS4 compared with VRS1.

In the first phase of angiogenesis (i.e., progression from VRS1 to VRS2), the relative increase in density of small arteries (G≥6) by Lv and Nv was larger than the relative increase of small veins (FIG. 16). However, results were opposite for the second, late-stage phase of angiogenesis/neovascularization (progression from VRS3 to VRS4), when the relative increase in density of small veins exceeded that of small arteries. Furthermore, the final overall increase in Dv of large- and medium-sized veins (G1-5) from VRS1 to VRS4 was greater than that of large- and medium-sized arteries (12% compared to 6%; FIG. 17). Together, these two results for vessel density and vessel diameter may suggest a fundamental switch in the second, more severe phase of late-stage angiogenesis from a vascular phenotype of arterial-dominated remodeling to a phenotype of venous-dominated remodeling.

The major result of this study was the oscillation (alternation) of increasing and decreasing density of small blood vessels, as mapped and quantified by Lv and Nv, in both arterial and venous trees during progression of diabetic retinopathy from mild to very severe non-proliferative diabetic retinopathy/early PDR. When classified by VRS, the density of smaller vessels increased from VRS 1 to VRS2, decreased from VRS2 to VRS3, and increased again from VRS3 to VRS4, as quantified by using the VESGEN system with strong statistical confidence. The two phases of increased vessel density (VRS1 to VRS2 and VRS3 to VRS4) were dominated first by arterial remodeling and were followed by venous remodeling, although progressive change was always positively correlated between arterial and venous trees. Classification of VRS by vessel density correlated significantly with ranking by clinical diagnosis from mild non-proliferative diabetic retinopathy to very severe non-proliferative diabetic retinopathy/early PDR (13/15 eyes). Indeed, vessel densities for the two uncorrelated retinas (eyes 8 and 13) correlated positively with the next phase of retinopathy progression, suggesting that vascular remodeling may be an earlier prognosticator of retinopathy status than secondary vascular effects, such as microaneurysms and hemorrhages.

Throughout the progression of diabetic retinopathy, the density of larger vessels (G1-5) remained relatively unchanged, and the diameters of larger vessels (Dv1-5) increased slightly but consistently. Fluorescein angiography images may be used because of the superior resolution of the critically important smaller blood vessels in comparison with fundus images. This analysis may also prove useful for good quality fundus images.

Inspection of the mappings from the VESGEN system and binary vascular trees (FIGS. 11-14) reveals that changes throughout the retinal vasculature displayed in a fluorescein angiography image are not necessarily uniform with progression of diabetic retinopathy. Therefore, increased vessel density as net angiogenesis, neovascularization, or both and decreased vessel density as net vascular dropout were described. Vascular change from very severe non-proliferative diabetic retinopathy to PDR may be characterized by neovascularization with increased numbers of vessel structures (primarily venous intraretinal microvascular abnormalities) that may be organized as vascular loops rather than by tapered branching. The oscillation between angiogenesis/neovascularization and vascular dropout with the progression of diabetic retinopathy may suggest that the diabetic retina retains the capacity to recover a normal vascular phenotype to some extent during earlier stages of retinopathy. Presumably, the cyclical nature of the angiogenesis/vascular dropout process is regulated by competing provascular and antivascular factors such as tissue hypoxia, VEGF, and other stimulatory and inhibitory factors.

In a previous study based on fractal analysis, it was found that vessel density decreased in the mild non-proliferative diabetic retinopathy macular region compared with the normal macula. If the results reported for the present study, using the VESGEN system, of arterial and venous trees are consistent with results for the previous fractal study of overall vessel density, then the increased vessel density of the moderate non-proliferative diabetic retinopathy retina would resemble more closely the vascular architecture of the normal, healthy retina than the mild non-proliferative diabetic retinopathy retina. Vascular dropout in mild non-proliferative diabetic retinopathy may be the initial phase of significant ischemic injury. Answers to the question—whether retinal vessels drop out during mild non-proliferative diabetic retinopathy and recover (regenerate) to some extent during moderate non-proliferative diabetic retinopathy—may be critical for advances in therapeutic design. By way of a non-limiting example, drugs that ameliorate tissue hypoxia, vascular dropout, or early angiogenesis may potentially reverse the progression of diabetic retinopathy during early stages more favorably than in the later stages, when anti-VEGF and other antiangiogenesis therapies are tested.

It is not surprising that oscillation of vessel density with progression of diabetic retinopathy depends primarily on the alternating growth and dropout of smaller, more fragile blood vessels. Research has shown that factors such as VEGF and normoxia are required to stabilize and maintain the smaller blood vessels. Moreover, the molecular and cellular characteristics of angiogenic and remodeling vascular tissues differ from those of more mature, stable vascular tissues. As shown by the analysis from the VESGEN system of numerous growth factors and therapeutics in chorioallantoic membrane, stimulation or inhibition of angiogenesis targets the small blood vessels within the vascular tree.

Despite the generality of inhibition and stimulation at the level of small vessels, each molecular perturbant of angiogenesis elicited a response that was spatiotemporally distinct and quantifiable. Previous studies of vascular remodeling using the analysis from the VESGEN system in the avian chorioallantoic membrane experimental model have focused mainly on the mapping and quantifying of unique "fingerprint" or "signature" patterns induced by angiogenic stimulators such as VEGF165 and bFGF, and by inhibitors such as TGF-$\beta$1, angiostatin, and the steroid TA. Results of the chorioallantoic membrane studies suggest the hypothesis that progressive changes in the vascular patterns of pathologic angiogenesis and human vascular diseases such as diabetic retinopathy may be analyzed to determine whether molecular signature patterns can be identified that provide informative integrative readouts of the dominant molecular signaling.

In the present study, for example, the switch from the high arterial density and relatively normal diameters of larger arteries at VRS2 (as correlated with moderate non-proliferative diabetic retinopathy) to lower arterial density and significantly increased diameters of larger arteries at VRS4 (correlated with very severe non-proliferative diabetic retinopathy/early PDR) corresponds morphologically to changes mapped and quantified by the VESGEN system for VEGF regulation. Vessel density in the chorioallantoic membrane increased at low concentrations of VEGF. With higher concentrations of VEGF, however, the vascular phenotype displayed progressively decreasing vessel density and increasing diameters of larger arteries. Adverse side effects of TA as a therapeutic agent for vascular retinopathies, such as increased risk for glaucoma, may result from the unfavorable thinning of vessel diameters, as demonstrated by experimental results for TA measured by the VESGEN system in the chorioallantoic membrane. Finally, the effects of drugs on retinal vascular pattern may be evaluated by the VESGEN system to help quantify the degree of vascular normalization achieved by these therapeutics.

In other embodiments, the VESGEN system may be capable of mapping and analyzing venation branching patterns in plant leaves such as *Arabidopsis thaliana*. In these embodiments, change in vascular branching pattern may provide an informative read-out of alterations in complex regulatory signaling pathways. By way of a non-limiting example, alterations of venation pattern in the leaves of plants flown on the International Space Station such as *Arabidopsis thaliana* may be analyzed by the VESGEN system. Terrestrial leaf venations display valuable, genetically and environmentally determined 'signature' patterns that, when mapped and quantified, may contribute to fundamental and applied botanical systematics.

The VESGEN system analyzed plant leaves by analyzing venation patterns at Day 2 and Day 8 from *Arabidopsis thaliana* seedlings grown terrestrially. Leaf size increased greatly during maturation from Day 2 to Day 8; see FIG. 18e. Venation patterns within the leaves were binarized by semi-automatic image processing (see FIG. 18) described in more detail above. The black/white vascular pattern and its region of interest were analyzed automatically by the VESGEN system using the Vascular Tree-Network Composite option. Vessels within the branching tree-network composites were grouped into successively smaller generations of venous branching, according to recently established botanical geometric rules for a functional Morphology classification of branching vein orders (generations) in cotyledon leaves. The VESGEN system further mapped the vascular patterns into two groups of large structural veins (Orders 1°-2°) and small reticular veins (≥3°); see FIG. 18.

Figure 18:
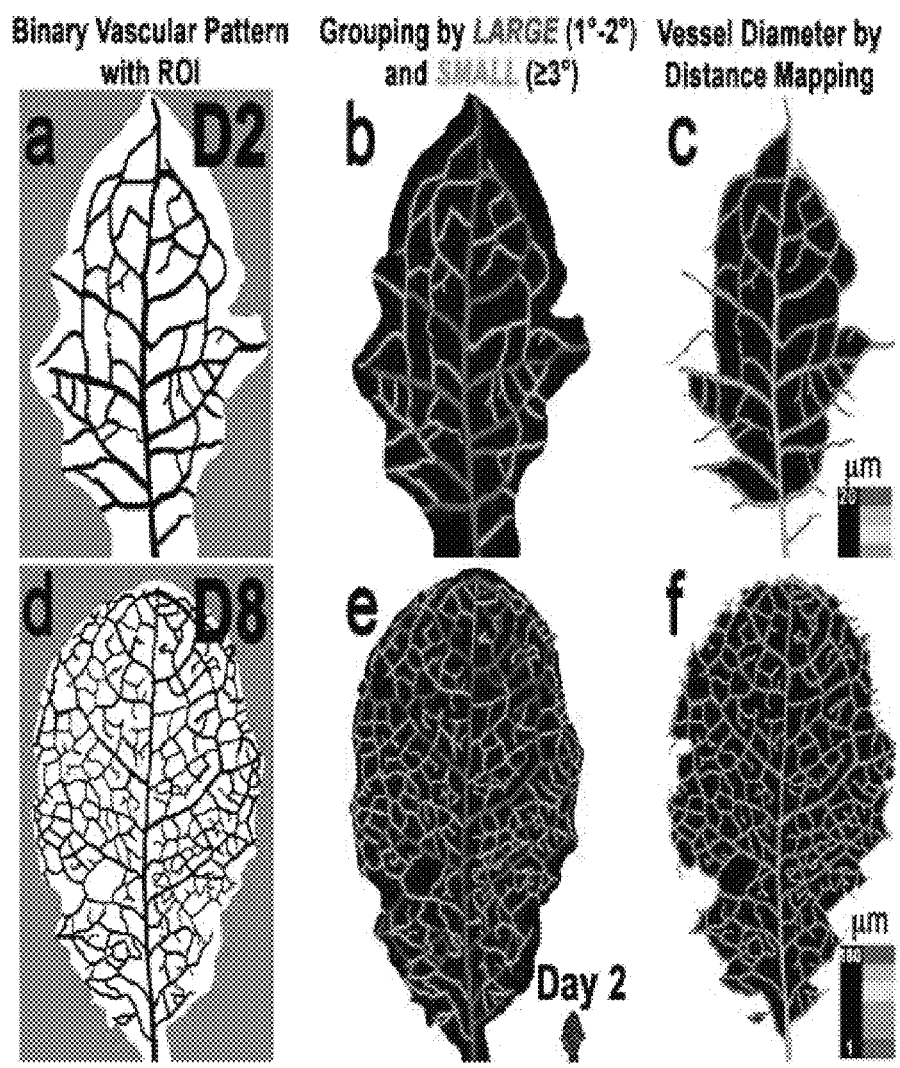
FIG. 18 are exemplary images from some embodiments of a VESGEN system of mapping of developing leaf venation pattern depicting binary vascular pattern with region of interest, grouped mapping by large and small structural veins and small reticular veins, and vessel diameter by distance mapping.

As shown in FIG. 18, binary vascular patterns (a, d) extracted from microscopic images of terrestrially grown *Arabidopsis thaliana* leaves at Day 2 (D2) and Day 8 (D8) may be analyzed by the VESGEN system. To provide useful quantification, the binary vascular patterns (see FIG. 18a, d) may be mapped as large structural, branching (1°-2°) veins and small reticular, networked veins (≥3°; see FIG. 18b, e) according to established rules of leaf venation architecture. Other venation groupings determined by branching orders are available to the User in the VESGEN system. Note the large increase in leaf size from Day 2 to Day 8 (see FIG. 18e). In addition, the VESGEN system representation (see FIG. 18c, f), for example, distance mapping displays the local thickness of vessel diameter throughout the vascular tree¬ network composite. Black indicates avascular spaces enclosed by, and quantified for, the tree-network structures. The VESGEN system may, therefore, allow for a generally more complete leaf venation branching analysis.

Vascular groups were determined by the VESGEN system according to established rules for leaf venation patterning, in which the large structural, branching veins are of primary (1°) and secondary (2°) order and the smaller net-worked veins forming the reticulum, of tertiary or greater (≥3°)

order. In the ordering of large structural vessels for dicotyledon leaves such as *Arabidopsis thaliana*, 2° (costal) veins branch from the single, central 1° vein. Veins of order ≥3° branch primarily from 2° veins to fill intercostal gaps between the roughly parallel 2° veins. Venation patterns in dicotyledon (dicot) leaves (pinnately and palmately veined) are therefore organized as tree-network composites, in which large structural veins form the hierarchical vascular branching tree and small reticular veins form the intercostal vascular network or net.

Using the VESGEN system analysis, leaf venation pattern matured considerably in branching complexity during leaf development. As a sensitive measure of branching complexity and space-filling capacity, the fractal dimension (Df) of the entire skeletonized branching pattern increased from 1.32 at Day 2 to 1.47 at Day 8. The ratio of vessel density (Av) for small reticular vessels to large structural vessels increased from 1.16 at Day 2 to 1.51 at Day 8. From Day 2 to Day 8, the average diameter (Dv, also termed vein gauge) of large structural vessels increased from 14.0 μm to 100.9 μm and Dv of small reticular vessels, from 9.3 μm to 70.0 μm. Other venation parameters measured by the VESGEN system may include vessel branch point density, vessel end point density, vessel length density and network analysis of avascular spaces, and overall vascular patterning that may include relative densities and branching completeness of lower-order structural veins compared to higher-order reticular veins, and bioinformatics such as cell receptor characteristics, gene expression, and environmental responses of leaf venation.

As a feasibility study, results of the VESGEN system analysis generally correspond to the botanical rules for large structural (1°-2°) and small reticular (≥3°) vessels. Discrepancies between these rules and the quantitative assessment may result from: 1) the immature state of the developing *Arabidopsis thaliana* venation patterns, which is consistent with pattern irregularities in developing animal vasculature, 2) insufficient image resolution and 3) current VESGEN system mapping limitations. In addition, the VESGEN system mapping capabilities may be generally optimized for improved detection of specific dicot leaf venation attributes such as branching angle and vessel tapering that differs somewhat from human and animal vascular branching.

Some embodiments of the present invention pertain to vascular patterning that facilitates the coordination of essentially unlimited numbers of bioinformatics dimensions for specific molecular and other co-localizations with spatiotemporal dimensions of vascular morphology, and/or that applies geometric principles of translational versus rotational principles for vascular branching to support the transformation of VESGEN 2D to VESGEN 3D. Virtually unlimited numbers of bioinformatic dimensions of single molecular expression including, but not limited to, gene expression, protein expression, hormones, miRNA, etc. may be co-localized with the previous VESGEN systems analysis of branching vessel morphology by spatial (geometric) and temporally evolving (dynamic) dimensions. A bioinformatic dimension of molecular expression may be defined as the expression pattern of a molecule, such as a protein, or a sub-molecular moiety, such as a gene (i.e., the unit of genetic heredity), within a tissue that can be imaged within a 2D plane or 3D volume. Generally, patterns of molecular expression can be quantified by a range in intensity or density of expression such as, for example, 0 to 255 levels of gray. Such bioinformatic dimensions of molecular expression may be co-localized with, or largely external to, other structures, such as the vascular system. The co-localized relationship between molecular expression and a specialized functional system, such as the vasculature, generally has important significance for cell signaling and other functions of the molecule or molecular moiety. An advantage of the site-specific VESGEN system analysis is therefore that expression of VEGF or other regulatory molecules may vary considerably at different generational branching sites within the vascular trees. Geometric principles of translational versus rotational principles for vascular branching to support transformation of VESGEN 2D to VESGEN 3D are also disclosed.

VESGEN is relevant to remodeling vascular systems of the five major metazoan models of the modem omics revolution, as well as to human clinical diagnostic imaging. These experimental models, of critical importance because of their relative ease of genome manipulation by laboratory genetic engineering studies, include the mouse (*Mus musculus*), zebrafish (*Danio rerio*), nematode (*Caenorhabditis elegans*), fruit fly (*Drosophila melanogaster*), and thale cress (*Arabidopsis thaliana*). Only *C. elegans* lacks a vascular system. VESGEN has therefore been requested or applied for vascular discovery applications to all four remaining experimental models. For example, VESGEN was disclosed for application to venation patterning in the fruit fly wing in November of 2014. The wing and other fruit fly tissues are often important for initial immunity and therapeutic discoveries in biomedical research because approximately 70% of human disease genes closely match genes within the fruit fly genome. The VESGEN analysis also appears useful for ecology and other studies in the leaves of higher land plants due to similar branching principles that determine vertebrate vascular branching and leaf venation, such as the generalized principle of vascular branching by vessel bifurcation. Leaf venation is critically involved in the process of photosynthesis, and is therefore fundamental to oxygen-carbon exchanges on Earth and in human habitats for long-duration space exploration. In addition, the recent revolutionary CRISPR technology will make the vascular systems of many more organisms amenable to the combined VESGEN vascular/bioinformatics analysis.

Physiological branching principles innovatively utilized by VESGEN are summarized as follows. Vertebrate vascular branching is almost invariably bifurcational (i.e., not trifurcational, etc.). Vessels invariably taper except in unusual circumstances such as extreme pathologies, wound-healing or early development. The rule also appears to apply to invertebrate vascular branching in the fruit fly wing and *Arabidopsis* leaf. Two types of vessel branching events are observed in tissues of even moderate vascular complexity, such as the human and other vertebrate retinas and avian CAM and coronary vessels: (1) offshoot vessels, in which vessels of much smaller diameter branch off from a vessel of much larger diameter; and (2) offspring vessels (also denoted child or daughter vessels) in which diameters of two approximately equal offspring vessels branch symmetrically from the parent vessel.

Due to the fluid mechanics of laminar blood flow for vertebrates, in which the blood and fragile blood cells are circulated by a pumping heart, the diameters of the offspring vessels are approximately 70% of the diameter of the parent vessel. For the VESGEN analysis, this rule is the major, most highly weighted determinant of a new, successively branching generation assignment. However, the biology of vascular patterning is much more complex than would be determined by this single branching rule (which would be sufficient to specify a mathematical algorithm of self-similar fractal branching). Inspection of retinal and CAM vascular images analyzed by VESGEN readily reveals that vertebrate biological branching appears to be a complex combination of deterministic and random-like branching events. A curious, fundamental, long-term finding of the VESGEN research program in several models, such as the cytokine-perturbed quail CAM and progression of diabetic retinopathy, is that each vascular pattern in an individual CAM specimen or human retina is unique, like a human fingerprint.

Nevertheless, when quantified by VESGEN, the fractal-based space-fitting properties of such vascular patterns within a single population or treatment class are remarkably uniform (i.e., group variation is low and statistical significance is high). The space-filling uniformity of individually unique vascular patterns in vertebrates contrasts with the stereotyped vascular patterning in the *Drosophila* wing, for example. Presumably the biological result for vertebrate vascular patterning stems from uniform tissue demands for oxygen and other metabolic factors. It is further hypothesized that the strong statistical significance within population groups results in part from the large sampling number, because generally, large numbers of vessels are contained within such tissues. Of course, an underlying requirement for the strong reproducibility of the VESGEN analysis is consistency in the microscopic and clinical imaging methods.

Some embodiments of the present invention incorporate functional information dimensions (functional bioinformatics) by which the pattern of expression of a single gene, protein, or other molecule is co-localized with the vascular maps within VESGEN to advance understanding of functional vascular patterning. Some embodiments also use sophisticated data mining to identify functional relationships from modern biology's molecular profiling with multi-omic datasets. Complex, fractal-based branching vascular systems are ubiquitous among all higher terrestrial organisms that include humans, other vertebrates, insects, and plants. Hence vascular patterning offers a powerfully innovative biomarker read-out that necessarily integrates complex signaling by tens of thousands of interacting molecules. The Human Genome Project (still under development) resulted in databases containing 20,000-25,000 protein-coding genes, and associated proteome efforts are underway to map proteins of the human body, estimated at approximately 30,000 to 50,000 in number.

Some embodiments directly address challenges of human health and medicine, and even vehicle environmental design, which is fundamental to long-duration space exploration. Image maps of molecular expression may be integrated as information dimensions with co-localized Euclidean vascular maps to generate VESGEN bioinformatics. Vascular research, and biological research in general, require image maps displaying the localized expression of functional signaling molecules, such as growth factors for interpretation of molecular significance with their associated omics data. See mappings 100 of FIG. 19A.

Furthermore, the morphological architecture of vascular systems transporting blood and other blood-like fluids must follow physical laws of fluid dynamics and transport phenomena such as aqueous continuity to accomplish their communications function. The VESGEN bioinformatics platform in some embodiments integrates functional molecular expression maps and omics with Euclidean vascular form.

Data mining algorithms in some embodiments linking omics datasets identifying changes in gene, protein, RNA, or other expression profiles will integrate the PCR-based chemistry of these genotypic omic datasets with phenotypic functional (function-identifying) bioinformatics VESGEN to create new systems software of integrated vascular form and function. Images that map the expression of single molecules onto morphological structures, such as vascular systems, provide critical evidence for identifying key molecules that participate in tissue function and remodeling. However, to screen more accurately for complex regulatory signaling, large omics databases that have tested the chemical expression profiles of large numbers of molecules (genes, proteins, etc.) are currently important for use in conjunction with image maps of localized molecular expression described above. This is because localized maps of molecular expression are required to reveal and consequently understand the anatomical localization and function of these molecules. For example, breakthrough therapeutics, such as vascular inhibiting drugs effective against blindness and tumors, were identified by this experimental approach. Specially designed data mining techniques for heterogeneous data combine concepts in clustering, kernel learning, and machine learning to analyze the functional omics datasets with structural and functional vascular data already contained within VESGEN.

Figure 19A:
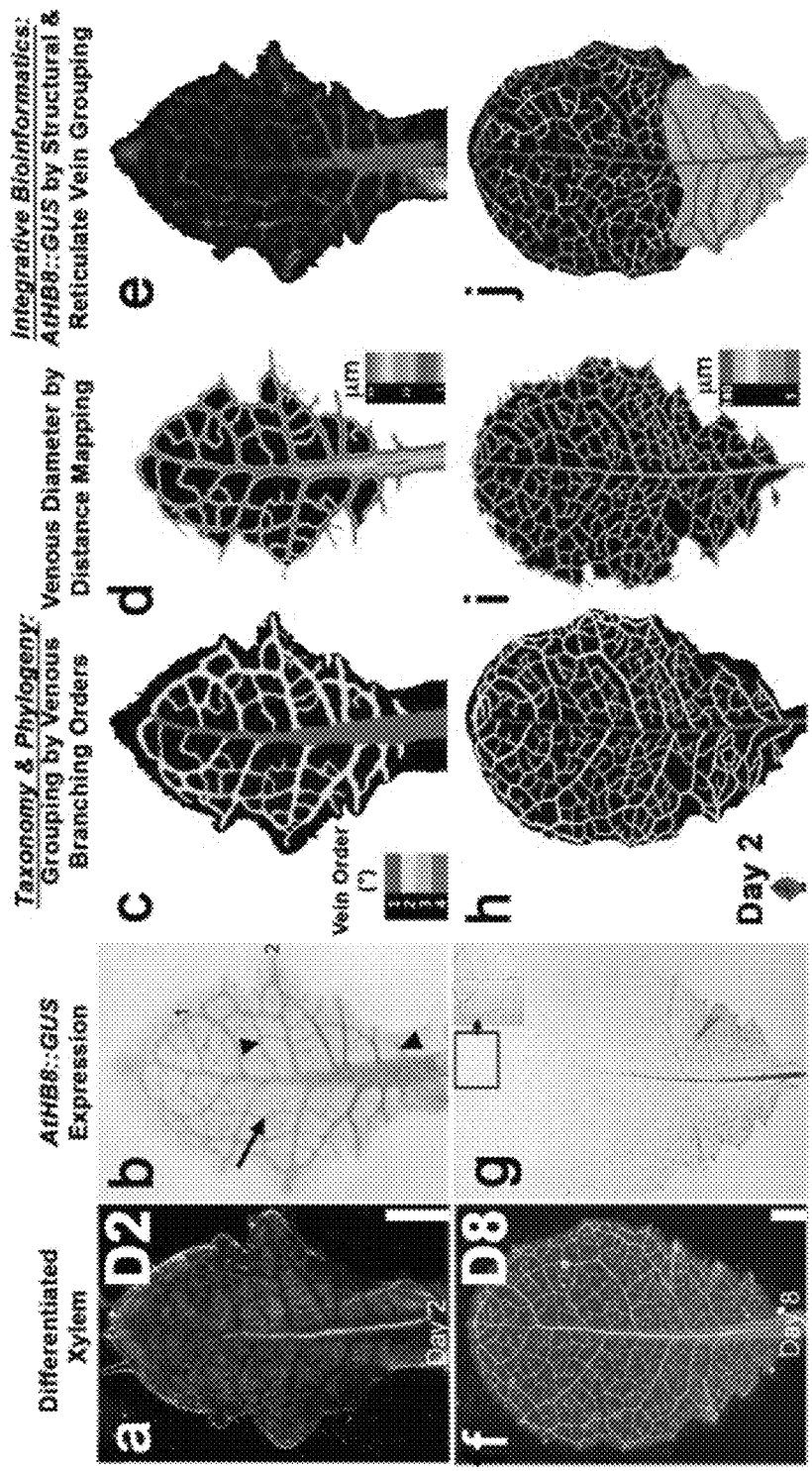
FIG. 19A illustrates VESGEN mappings of leaf venation co-localized with protein expression (AtHB8::GUS) of a single vascular regulatory gene according to an embodiment of the present invention.
Figure 19B:
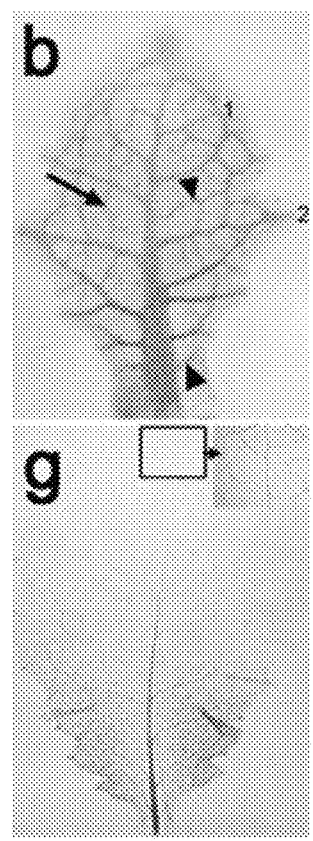
FIG. 19B is a magnified view of images b and g from FIG. 19A with darkened contrast, according to an embodiment of the present invention.

In FIG. 19A, innovative VESGEN assignment of vascular branching generations based on physiological rules is illustrated by branching generations G. Images b-e are derived from image a, and images g-j are derived from image f Expression of growth factor *Arabidopsis* homeobox gene-8 (AtHB8::GUS—see images b, g) was co-localized with the vascular patterns in images e, j and quantified. Images b, g are more clearly seen in FIG. 19B.

Patterns of differentiated xylem a, f with AtHB8::GUS expression b, gin the normally developing *Arabidopsis* adult leaf (Leaf 8) at Day 2 (D2) and Day 8 (D8) of normal development reproduced from a study by Kang and Dengler (2004) were mapped by VESGEN software in images c-e, h-j.

Images c, e show large structural veins (orders 1° and 2°) and small reticular veins (3° and ≥4°) were mapped with botanical rules summarized in FIG. 19. Note the large increase in leaf size and vascular expansion from Day 2 to Day 8 in image h. Euclidean distance mapping by VESGEN in images d, i quantifies the local thickness of vessel diameter throughout the vascular tree-network composite. Black indicates enclosed avascular spaces. To demonstrate the proposed VESGEN bioinformatic capability, the time-dependent localized expression of HD-Zip class III transcription factor AtHB8::GUS (images b, g) was mapped into vascular patterns automatically grouped by VESGEN into structural (1° to 2°) and reticulate (3° to 4°) vein orders in images e, j.

The mapping for Day 2 in image e displays the local intensity of AtHB8::GUS expression throughout the leaf lamina as a function of the venation architecture and vessel branching order illustrated in image c. Intensity levels from 0 to 255 (red channel of RGB) quantify AtHB8::GUS expression localized within structural veins of orders 1° to 2°; red levels from 0 to 255 within reticulate veins of orders 3° to 4°, and gray intensity levels, to AtHB8::GUS expression within the extravascular leaf lamina (intensities brightened for visibility). AtHB8::GUS expression at Day 8 in image j is now restricted to the still-expanding basal region. In image b, "1" denotes the first-formed secondary vein loop; "2" denotes the second-formed secondary vein; the black arrowheads denote intercalated secondary veins; the black arrow denotes a smaller-diameter "connector" joining adjacent secondary vein. In image g, the inset shows absence of AtHB8::GUS expression from the leaf apex. The bar in image a denotes 200 µm and the bar in image f denotes 1 mm.

Per the above, the VESGEN system analysis of vascular patterning has been expanded in some embodiments to include essentially unlimited bioinformatic dimensions of single molecular expression including, but not limited to, gene expression, protein expression, hormones miRNA, etc. as co-localized with the spatial (geometric) and temporally evolving (dynamic) dimensions of branching vessel morphology. An advantage of the site-specific VESGEN system analysis is therefore that expression of VEGF or other regulatory molecules often varies considerably at different generational branching sites within the vascular trees. Coordination of combinatorially large numbers of omics profiling in changes of genetic and other molecular expression with specific molecular and other co-localizations together with the spatiotemporal dimensions of vascular morphology is a powerful new tool for informative interactions in modern biological omics (genomics, proteomics, exosomics, etc.). Per the above, the protein expression of the vascular growth modulator AtHB8::GUS is used within the growing venous tree in leaves of the plant genetic model organism, *Arabidopsis*. Because of the universality of cell biology principles for genetic and protein translational codes, the VESGEN bioinformatic system of vascular patterning demonstrated with vascular remodeling in the *Arabidopsis* leaf is immediately transferrable to vascularized metazoans of the animal kingdom.

Vascular complexity increased during normal terrestrial maturation of adult an *Arabidopsis* leaf by fractal-based measures of venation geometry in association with progressively modulating expression of the *Arabidopsis* vascular growth regulator, AtHB8::GUS. By the fractal dimension (Df), the space-filling capacity of the leaf vascular pattern increased from 1.38 at Day 2 to 1.47 at Day 8. See FIGS. 19A and 19B. The numbers (Nr) of reticulate veins increased from 51 to 255, respectively, and Nr of structural veins increased from 68 to 153. At Day 2, the average intensity of the bioinformatic histogram analysis for AtHB8::GUS co-localization for grouped structural orders (1-2) was 86±52 (mean±SD, 256 gray levels), and 40±20 for grouped reticulate orders (≥3). The co-localized expression of AtHB8::GUS could not be mapped into the veins at Day 8 because the source journal image of AtHB8::GUS localization did not quite overlap with the image of venation patterning. However, to illustrate a second type of useful bioinformatic analysis, the basal location of AtHB8::GUS expression was successfully estimated and mapped as highly restricted by Day 8 to 29% of the total vascular area, compared to 100% at Day 2.

From the above results, a VESGEN ensemble that combines dimensional parameters of vascular geometry with bioinformatic dimensions of co-localized gene, protein, and other molecular expression can be formulated as:

$$f,g=\{[f1,i,f2,i,\ldots],[g1,i,g2,i,\ldots]\} \quad (1)$$

where the vector functions f and g consist of dynamic (i.e., time-dependent) two-dimensionally or three-dimensionally co-localized information. The set f contains parameters of vascular morphological geometry, such as Df and Nv, that further allow for parameter specification to successive branching generations of i=1, j=2, etc., as well as to vascular and avascular zones within the tissue. Similarly, the vector function g includes the bioinformatic set of co-localized molecular expression patterns. Results for the adult *Arabidopsis* leaf at t=Day 2 of development in FIGS. 19A and 19B can now be expressed as:

$$f,g=\{[Df,(Nv1-2,Nv\geq3)],[AtHB8::GUS1-2,AtHB8::GUS\geq3]\} \quad (2)$$

in which f1=Df; f2,1-2=Nv1-2, and f2, ≥3=Nv≥3, where f2,1-2 is the vessel number density in structural veins of orders 1-2 (analogous to vertebrate branching generations 1-2), and f2, ≥3=Nv≥3, vessel number density in reticulate veins of orders 3 and greater. Many other parameters of vascular morphological complexity, such as vessel diameter, length, and densities of branch points and end points can be included in f. For co-localized expression of the molecular marker AtHB8::GUS in structural and reticulate veins of orders 1-2 and ≥3, g1,1=AtHB8::GUS1-2 and g1,2=AtHB8::GUS≥3, respectively. Vast numbers of other bioinformatic molecular expression can be combined with vascular geometric information within the VESGEN systems ensemble, such as g2,i for the *Arabidopsis* growth factor ARF19. For practical applications, the actual numbers of bioinformatic dimensions of gene, protein, and other co-localized expression factors are currently limited by experimental practices such as fluorescent labeling of specific molecules and microscopic/imaging techniques.

In general, organ-specific and tissue-specific vertebrate vascular systems are organized as described below. The space-filling, vascular branching principles appear optimally designed to transport to and from each cell the metabolic, immune, and functional factors necessary for cell survival and tissue-specific function. These fractal-based principles can also be observed in non-vertebrate tissues, such as the Drosphila (fruit fly) wing and *Arabidopsis* leaf. The vascular branching rules are employed to create the VESGEN 3D software in some embodiments. It is anticipated that the VESGEN 3D software is geometrically a straightforward extension of the VESGEN 2D vascular branching analysis principles. While technically difficult in terms of implementing the imaging analysis for 3D image stacks, the 3D branching analysis principles of 26-neighbor voxel connectivity (instead of 2D 8-neighbor pixel connectivity) and mapping comparisons of skeletonizing, distance mapping, and trimmed skeleton analysis, remain the same. Some vascularized tissues, such as the vertebrate retina, dicot plant leaf, and avian CAM, are successfully approximated by a 2D vascular analysis. However, most organs and tissues in the body, such as the brain, liver, heart, and kidney, are 3D structures that cannot be analyzed from 2D images. Geometric principles of translational versus rotational symmetries are used to analyze these complex 3D vascular branching structures.

Major parent vessels, such as a one or several major arteries and veins, enter an organ or tissue reinforced by a structure, such as the hilum in the liver, lymph node, and kidney, optic nerve in the retina, and lignin sheathing of the first order (parent) structural vein in the *Arabidopsis* leaf. Vessels bifurcate successively within these (asymmetric) branching vascular trees until reaching the level of the (symmetric) endpoint capillary or end-veinlet reticulate networks, the site of chemical transfers with a tissue's specialized functional cells. In general, geometric principles of translational versus rotational symmetries and asymmetries can be used to begin analyzing such 3D structures. An example of useful vascular translational asymmetry in the human retina is the radial prepapillary, inner and outer retinal capillary layers extending in the z-direction, connected by arterioles and venules to the (slightly curved) x,y plane of the arterial and venous retinal trees. An example of useful vascular translational symmetry is intravital confocal images of the mouse luminal microvasculature in an inflammatory disease model in Parsons-Wingerter P., Reinecker H. C., "For Application to Human Spaceflight and ISS Experiments: VESGEN Mapping of Microvascular Network Remodeling during Intestinal Inflammation," Gravitational Space Biology 26(2):2-12 (2012). The VESGEN 2D application to (slightly 3D) intestinal confocal images is further described in Chen X., Yang G., Song J. H., Xu H., Li D., Yang X., Zeng H., Parsons-Wingerter P. A., Reinecker H. C., and Kelly C. P., "Probiotic Yeast Inhibits VEGFR Signaling and Angiogenesis in Intestinal Inflammation," PloS One 8(5):e64227 (May 13, 2013). Collaboration was with Massachusetts General Hospital and Harvard Medical School for both publications. In the inflammatory disease model, the primarily x,y planar structure of the vascular network is slightly curved and extended into the z-direction. Examples of 3D rotational vascular symmetry include the pre-capillary vascular trees of the mammalian liver and kidney.

Further applications of the vascular branching systems analysis encompassed by the VESGEN systems approach include not only current clinical ophthalmology imaging technologies to vision-impairing retinal vascular disease such as fluorescein angiography and specialized mydriatic and non-mydriatic camera imaging, but also current research methods not yet widely used in clinical practice that include new 3D imaging technologies such as adaptive optics scanning laser technology (AOSLO) and OCT angiography. The VESGEN vascular analysis can also be usefully combined with the "dissection" of the role of vascular branching to the fluid mechanics of laminar blood flow using the Doppler approaches of particle imaging velocimetry (PIV) and laser Doppler OCT angiography.

Figure 20:
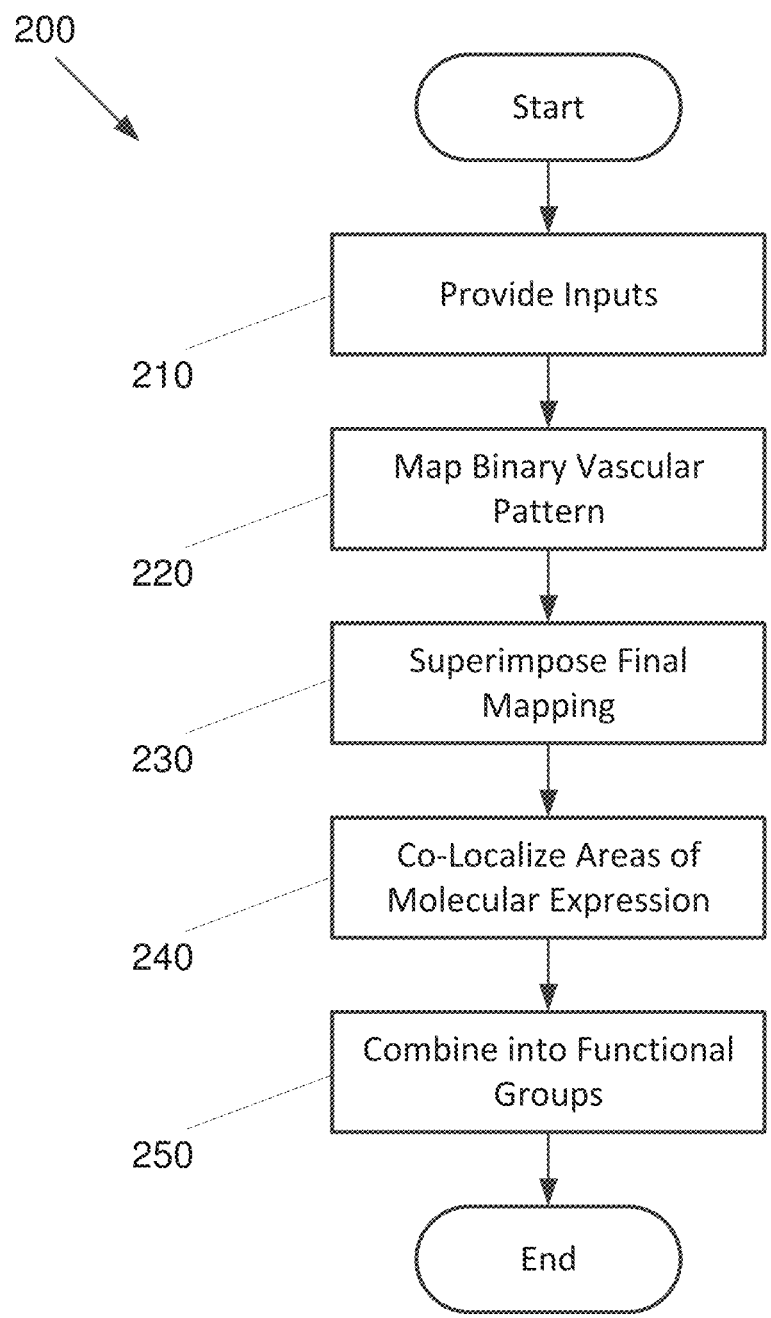
FIG. 20 is a flowchart illustrating a process for vascular patterning, according to an embodiment of the present invention.

FIG. 20 is a flowchart 200 illustrating a process for vascular patterning, according to an embodiment of the present invention. The process begins with the user providing two inputs to the VESGEN Bioinformatics software at 210: (1) a binary map of a vascular pattern; and (2) a grayscale image of co-localized molecular expression. The binary vascular pattern is then mapped into branching generations by sequential creation, and then coordinate analysis, of a series of image transformations that include the vascular skeleton, Chamfer thin filament distance map transforms determining local vessel diameter, and a trimmed skeleton that identifies specific vessels for generation assignments at 220. The final mapping of specific vessel generations is then superposed onto the grayscale image of co-localized molecular expression to assign regions of molecular expression to specific vascular branching generations, as well as to avascular areas within the tissue, at 230. For example, some factors such as stimulators or inhibitors of vessel growth may function primarily by spatial gradient signaling located outside of the vessels. Others, such as AtHB8::GUS in FIG. 19, are located primarily within the vascular structures.

The grayscale intensity of the areas of molecular expression co-localized to specific vessel branching generations are then analyzed by a histogram frequency approach that yields the mean and standard deviation of 256 levels of gray for each vessel and each vessel generation as a measure of comparative densities of molecular expression at 240. This co-localized analysis of molecular expression results in a density map of molecular expression specified to specific vessel branching generations. Vessels, and their combination into their respective vessel generations of co-localized molecular expression, are then often further combined into functional groups of vessels, such as small, medium, and large vessels illustrated in FIG. 19, as the large structural vessel orders (orders 1-2) and the smaller networked (reticulate, ≥3) orders.

Figure 21:
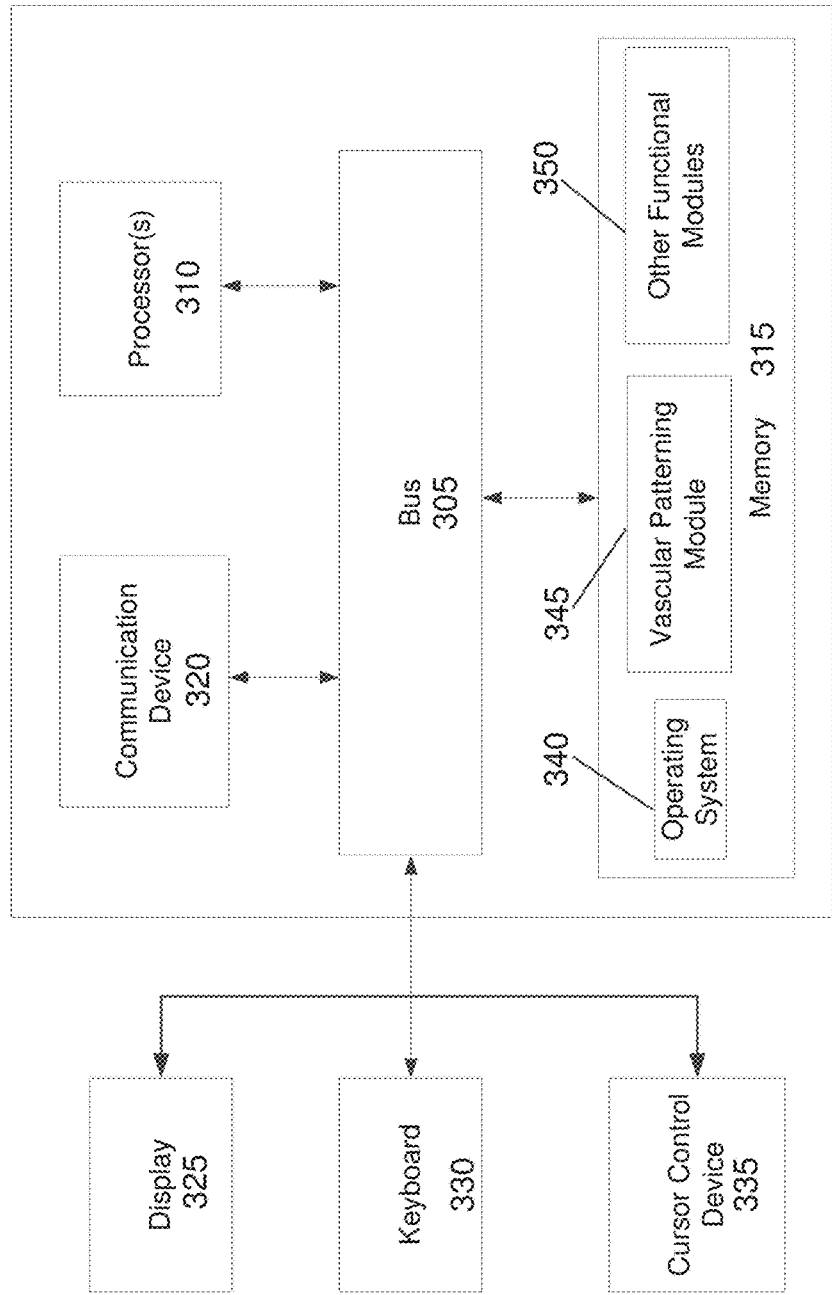
FIG. 21 is a block diagram of a computing system configured to perform vascular patterning, according to an embodiment of the present invention.

FIG. 21 is a block diagram of a computing system 300 configured to perform vascular patterning, according to an embodiment of the present invention. Computing system 300 includes a bus 305 or other communication mechanism for communicating information, and processor(s) 310 coupled to bus 305 for processing information. Processor(s) 310 may be any type of general or specific purpose processor, including a central processing unit ("CPU") or application specific integrated circuit ("ASIC"). Processor(s) 310 may also have multiple processing cores, and at least some of the cores may be configured to perform specific functions. Computing system 300 further includes a memory 315 for storing information and instructions to be executed by processor(s) 310. Memory 315 can be comprised of any combination of random access memory (RAM), read only memory (ROM), flash memory, cache, static storage such as a magnetic or optical disk, or any other types of non-transitory computer-readable media or combinations thereof. Additionally, computing system 300 includes a communication device 320, such as a transceiver and antenna, to wirelessly provide access to a communications network.

Non-transitory computer-readable media may be any available media that can be accessed by processor(s) 310 and may include both volatile and non-volatile media, removable and non-removable media, and communication media. Communication media may include computer-readable instructions, data structures, program modules or other data in a modulated data signal such as a carrier wave or other transport mechanism and includes any information delivery media.

Processor(s) 310 are further coupled via bus 305 to a display 325, such as a Liquid Crystal Display (LCD), for displaying information to a user. A keyboard 330 and a cursor control device 335, such as a computer mouse, are further coupled to bus 305 to enable a user to interface with computing system. However, in certain embodiments such as those for mobile computing implementations, a physical keyboard and mouse may not be present, and the user may interact with the device solely through display 325 and/or a touchpad (not shown). Any type and combination of input devices may be used as a matter of design choice.

Memory 315 stores software modules that provide functionality when executed by processor(s) 310. The modules include an operating system 340 for computing system 300. The modules further include a vascular patterning module 345 that is configured to perform vascular patterning in accordance with the embodiments discussed herein. Computing system 300 may include one or more additional functional modules 350 that include additional functionality.

One skilled in the art will appreciate that a "system" could be embodied as an embedded computing system, a personal computer, a server, a console, a personal digital assistant (PDA), a cell phone, a tablet computing device, or any other suitable computing device, or combination of devices. Presenting the above-described functions as being performed by a "system" is not intended to limit the scope of the present invention in any way, but is intended to provide one example of many embodiments of the present invention. Indeed, methods, systems and apparatuses disclosed herein may be implemented in localized and distributed forms consistent with computing technology, including cloud computing systems.

It should be noted that some of the system features described in this specification have been presented as modules, in order to more particularly emphasize their implementation independence. For example, a module may be implemented as a hardware circuit comprising custom very large scale integration (VLSI) circuits or gate arrays, off-the-shelf semiconductors such as logic chips, transistors, or other discrete components. A module may also be implemented in programmable hardware devices such as field programmable gate arrays, programmable array logic, programmable logic devices, graphics processing units, or the like.

A module may also be at least partially implemented in software for execution by various types of processors. An identified unit of executable code may, for instance, comprise one or more physical or logical blocks of computer instructions that may, for instance, be organized as an object, procedure, or function. Nevertheless, the executables of an identified module need not be physically located together, but may comprise disparate instructions stored in different locations which, when joined logically together, comprise the module and achieve the stated purpose for the module. Further, modules may be stored on a computer-readable medium, which may be, for instance, a hard disk drive, flash device, RAM, tape, or any other such medium used to store data.

Indeed, a module of executable code could be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network.

The process steps performed in FIG. 20 may be performed by a computer program, encoding instructions for the non-linear adaptive processor to perform at least the process described in FIG. 20, in accordance with embodiments of the present invention. The computer program may be embodied on a non-transitory computer-readable medium. The computer-readable medium may be, but is not limited to, a hard disk drive, a flash device, a random access memory, a tape, or any other such medium used to store data. The computer program may include encoded instructions for controlling the nonlinear adaptive processor to implement the process described in FIG. 20, which may also be stored on the computer-readable medium.

The computer program can be implemented in hardware, software, or a hybrid implementation. The computer program can be composed of modules that are in operative communication with one another, and which are designed to pass information or instructions to display. The computer program can be configured to operate on a general purpose computer, or an ASIC.

It will be readily understood that the components of various embodiments of the present invention, as generally described and illustrated in the figures herein, may be arranged and designed in a wide variety of different configurations. Thus, the detailed description of the embodiments of the present invention, as represented in the attached figures, is not intended to limit the scope of the invention as claimed, but is merely representative of selected embodiments of the invention.

The features, structures, or characteristics of the invention described throughout this specification may be combined in any suitable manner in one or more embodiments. For example, reference throughout this specification to "certain embodiments," "some embodiments," or similar language means that a particular feature, structure, or characteristic described in connection with the embodiment is included in at least one embodiment of the present invention. Thus, appearances of the phrases "in certain embodiments," "in some embodiment," "in other embodiments," or similar language throughout this specification do not necessarily all refer to the same group of embodiments and the described features, structures, or characteristics may be combined in any suitable manner in one or more embodiments.

It should be noted that reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention can be practiced without one or more of the specific features or advantages of a particular embodiment. In other instances, additional features and advantages may be recognized in certain embodiments that may not be present in all embodiments of the invention.

One having ordinary skill in the art will readily understand that the invention as discussed above may be practiced with steps in a different order, and/or with hardware elements in configurations which are different than those which are disclosed. Therefore, although the invention has been described based upon these preferred embodiments, it would be apparent to those of skill in the art that certain modifications, variations, and alternative constructions would be apparent, while remaining within the spirit and scope of the invention. In order to determine the metes and bounds of the invention, therefore, reference should be made to the appended claims.

The invention claimed is:

1. A computer-implemented method, comprising:
receiving two or more inputs comprising one or more binary maps of one or more vascular patterns, and one or more images of co-localized molecular expression;
mapping each of the one or more binary maps into vascular branching generations;
superimposing a final mapping of the vascular branching generations onto the one or more images of the co-localized molecular expression;
assigning, based on the superimposing, regions of the co-localized molecular expression to one or more specific vascular branching generations; and
analyzing, by a histogram analysis, intensities of the co-localized molecular expression of the assigned regions to quantify the co-localized molecular expression, wherein the step of analyzing the intensities yields a mean and a standard deviation of a plurality of levels of intensity for each vessel and for each vessel generation, wherein the plurality of levels of intensity are measures of comparative intensities of molecular expression.

2. The computer-implemented method of claim 1, wherein the mapping the each of the one or more binary maps into vascular branching generations comprises generating a vascular skeleton, Chamfer thin filament distance map transforms determining local vessel diameter, and a trimmed skeleton that identifies specific vessels for generation assignments.

3. The computer-implemented method of claim 1, wherein the plurality of levels of intensity comprise 256 levels of monochromatic intensity.

4. The computer-implemented method of claim 1, further comprising:
determining one or more values for one or more parameters of each vascular branching generation;
integrating a plurality of images of molecular expression with the one or more values for the one or more parameters of the co-localized vascular branching generations; and
generating bioinformatics from the integrating.

5. The computer-implemented method of claim 4, wherein the plurality of images of molecular expression comprise localized expression of functional signaling molecules.

6. The computer-implemented method of claim 5, wherein the localized expression of functional signaling molecules comprises growth factors for interpretation of molecular significance with associated omics data.

7. The computer-implemented method of claim 1, further comprising:
determining a plurality of values for a plurality of parameters of morphological geometry of each vascular branching generation;
designating one or more regions of interest for one or more of the plurality of values; and
determining the intensity of molecular expression co-located with a parameter exhibiting a value within a designated range.

8. The computer-implemented method of claim 1, wherein the one or more binary maps of one or more vascular patterns represent the vascular patterns at at least a first time and a second time.

9. The computer-implemented method of claim 1, wherein the one or more images of co-localized molecular expression represent the expression at at least a first time and a second time.

10. A computer program embodied on a non-transitory computer-readable device, the program configured to cause at least one processor to perform the steps of:
receiving two or more inputs comprising one or more binary maps of one or more vascular patterns and one or more images of co-localized molecular expression;
mapping each of the one or more binary maps into vascular branching generations;
superimposing a final mapping of the vascular branching generations onto the one or more images of the co-localized molecular expression;
assigning, based on the superimposing, regions of the co-localized molecular expression to one or more specific vascular branching generations; and
analyzing, by a histogram analysis, intensities of the co-localized molecular expression of the assigned regions to quantify the co-localized molecular expression, wherein the step of analyzing the intensities yields a mean and a standard deviation of a plurality of levels of intensity for each vessel and for each vessel generation, wherein the plurality of levels of intensity are measures of comparative intensities of molecular expression.

11. The computer program of claim 10, wherein the mapping of each of the one or more binary maps into vascular branching generations comprises generating a vascular skeleton, Chamfer thin filament distance map transforms determining local vessel diameter, and a trimmed skeleton that identifies specific vessels for generation assignments.

12. The computer program of claim 10, wherein the plurality of levels of intensity comprise 256 levels of monochromatic intensity.

13. The computer program of claim 10, wherein the program is further configured to cause the at least one processor to perform the steps of:
determining one or more values for one or more parameters of each vascular branching generation;
integrating a plurality of images of molecular expression with the one or more values for the one or more parameters of the co-localized vascular branching generations; and
generating bioinformatics from the integrating.

14. The computer program of claim 13, wherein the plurality of images of molecular expression comprise localized expression of functional signaling molecules.

15. The computer program of claim 14, wherein the localized expression of functional signaling molecules comprises growth factors for interpretation of molecular significance with associated omics data.

16. A computing system, comprising:
memory storing computer program instructions; and
at least one processor configured to execute the computer program instructions, wherein the instructions are configured to cause the at least one processor to perform the steps of:
receiving two or more inputs comprising one or more binary maps of one or more vascular patterns and one or more images of co-localized molecular expression;
mapping each of the one or more binary maps into vascular branching generations;
superimposing a final mapping of the vascular branching generations onto the one or more images of the co-localized molecular expression;
assigning, based on the superimposing, regions of the co-localized molecular expression to one or more specific vascular branching generations; and
analyzing, by a histogram analysis, intensities of the co-localized molecular expression of the assigned regions to quantify the co-localized molecular expression, wherein the step of analyzing the intensities yields a mean and a standard deviation of a plurality of levels of intensity for each vessel and for each vessel generation, wherein the plurality of levels of intensity are measures of comparative intensities of molecular expression.

17. The computing system of claim 16, wherein the mapping of each of the one or more binary maps into vascular branching generations comprises generating a vascular skeleton, Chamfer thin filament distance map transforms determining local vessel diameter, and a trimmed skeleton that identifies specific vessels for generation assignments.

18. The computing system of claim 16, wherein the plurality of levels of intensity comprise 256 levels of monochromatic intensity.

19. The computing system of claim 16, wherein the program is further configured to cause the at least one processor to perform the steps of:
  determining one or more values for one or more parameters of each vascular branching generation;
  integrating a plurality of images of molecular expression with the one or more values for the one or more parameters of the co-localized vascular branching generations; and
  generating bioinformatics from the integrating.

20. The computing system of claim 19, wherein the plurality of images of molecular expression comprise localized expression of functional signaling molecules.

* * * * *